United States Patent
Alten et al.

(10) Patent No.: US 10,527,623 B2
(45) Date of Patent: Jan. 7, 2020

(54) T CELL RECEPTORS AND IMMUNE THERAPY USING THE SAME

(71) Applicant: IMMATICS BIOTECHNOLOGIES GMBH, Tübingen (DE)

(72) Inventors: Leonie Alten, Tübingen (DE); Sebastian Bunk, Tübingen (DE); Dominik Maurer, Moessingen (DE); Claudia Wagner, Tuebingen (DE)

(73) Assignee: IMMATICS BIOTECHNOLOGIES GMBH, Tuebingen (DE)

( * ) Notice: Subject to any disclaimer, the term of this patent is extended or adjusted under 35 U.S.C. 154(b) by 0 days.

(21) Appl. No.: 15/835,095

(22) Filed: Dec. 7, 2017

(65) Prior Publication Data

US 2018/0164315 A1    Jun. 14, 2018

Related U.S. Application Data

(60) Provisional application No. 62/431,580, filed on Dec. 8, 2016.

(30) Foreign Application Priority Data

Dec. 8, 2016 (DE) .......................... 10 2016 123 859

(51) Int. Cl.
| | |
|---|---|
| *C07K 14/725* | (2006.01) |
| *G01N 33/574* | (2006.01) |
| *C07K 14/705* | (2006.01) |
| *A61P 35/00* | (2006.01) |
| *A61K 35/17* | (2015.01) |
| *A61K 39/395* | (2006.01) |
| *C07K 16/28* | (2006.01) |
| *G01N 33/58* | (2006.01) |
| *C07K 16/30* | (2006.01) |
| *A61K 39/00* | (2006.01) |

(52) U.S. Cl.
CPC .......... *G01N 33/574* (2013.01); *A61K 35/17* (2013.01); *A61K 39/0011* (2013.01); *A61K 39/39558* (2013.01); *A61P 35/00* (2018.01); *C07K 14/705* (2013.01); *C07K 14/7051* (2013.01); *C07K 16/2809* (2013.01); *C07K 16/30* (2013.01); *G01N 33/57492* (2013.01); *G01N 33/58* (2013.01)

(58) Field of Classification Search
None
See application file for complete search history.

(56) References Cited

U.S. PATENT DOCUMENTS

2016/0279215 A1     9/2016   Mahr et al.

FOREIGN PATENT DOCUMENTS

| EP | 2660250 A1 | 11/2013 |
|---|---|---|
| WO | 2014043441 A1 | 3/2014 |
| WO | 2015075939 A1 | 5/2015 |
| WO | 2016/011210 A2 | 7/2015 |
| WO | 2017089763 A1 | 6/2017 |

OTHER PUBLICATIONS

Janeway et al., Immunobiology, 5th Ed., Garland Science, 2001.*
Manning et al., Immunity, 8:413-425, 1998.*
Garcia et al, Cell, 122: 333-336, 2005.*
Miles et al, Immunol Cell Biol, 93:433-441, 2015.*
International Search Report issued in counterpart applicaiton No. PCT/EP2017/081893, dated Apr. 9, 2018.
Wang et al. "DCAF4L2 promotes colorectal cancer invasion and metastasis via mediating degradation of NFKb negative regulator PPM1B", Am J Transl Res 2016;8(2):p. 405-418.
German search report dated Dec. 12, 2016.

* cited by examiner

*Primary Examiner* — Mark Halvorson
(74) *Attorney, Agent, or Firm* — McBee Moore Woodward & Vanik IP, LLC

(57) ABSTRACT

The present invention relates to antigen recognizing constructs against a tumor associated antigen (TAA) derived from the target protein DDB1 and CUL4 associated factor 4-like 2 (DCAF4L2). The invention in particular provides novel T cell receptor (TCR) based molecules which are selective and specific for the TAA of the invention. The TCR of the invention, and TAA binding fragments derived therefrom, are of use for the diagnosis, treatment and prevention of TAA expressing cancerous diseases. Further provided are nucleic acids encoding the antigen recognizing constructs of the invention, vectors comprising these nucleic acids, recombinant cells expressing the antigen recognizing constructs and pharmaceutical compositions comprising the compounds of the invention.

9 Claims, 13 Drawing Sheets
(10 of 13 Drawing Sheet(s) Filed in Color)
Specification includes a Sequence Listing.

T CELL RECEPTORS AND IMMUNE THERAPY USING THE SAME

CROSS REFERENCE TO RELATED APPLICATIONS

This application claims benefit of U.S. Provisional Application Ser. No. 62/431,580, filed 8 Dec. 2016, and Great Britain Application No. 102016123859.7, filed 8 Dec. 2016, the content of which are incorporated herein by reference in their entireties.

This application is also related to PCT/EP2017/081893, filed 8 Dec. 2017, the content of which is incorporated herein by reference in its entirety.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2912919-080001_ST25.txt" created on 7 Dec. 2017, and 49,818 bytes in size) is submitted concurrently with the instant application, and the entire contents of the Sequence Listing are incorporated herein by reference.

Background

Field of the Invention

The present invention relates to antigen recognizing constructs against a tumor associated antigen (TAA) derived from the target protein DDB1 and CUL4 associated factor 4-like 2 (DCAF4L2). The invention in particular provides novel T cell receptor (TCR) based molecules which are selective and specific for the TAA of the invention. The TCR of the invention, and TAA binding fragments derived therefrom, are of use for the diagnosis, treatment and prevention of TAA expressing cancerous diseases. Further provided are nucleic acids encoding the antigen recognizing constructs of the invention, vectors comprising these nucleic acids, recombinant cells expressing the antigen recognizing constructs and pharmaceutical compositions comprising the compounds of the invention.

Description of Related Art

T-cell based immunotherapy targets represent peptide epitopes derived from tumor-associated or tumor-specific proteins, which are presented by molecules of the major histocompatibility complex (MHC). These tumor associated antigens (TAAs) can be peptides derived from all protein classes, such as enzymes, receptors, transcription factors, etc. which are expressed and, as compared to unaltered cells of the same origin, usually up-regulated in cells of the respective tumor.

Specific elements of the cellular immune response are capable of selectively recognizing and destroying tumor cells. The isolation of T-cells from tumor-infiltrating cell populations or from peripheral blood suggests that such cells play an important role in natural immune defense against cancer. CD8-positive T-cells in particular, which recognize class I molecules of the major histocompatibility complex (MHC)-bearing peptides of usually 8 to 10 amino acid residues derived from proteins or defective ribosomal products (DRiPs) located in the cytosol, play an important role in this response. The MHC-molecules of the human are also designated as human leukocyte-antigens (HLA).

There are two classes of MHC-molecules, MHC class I and MHC class II. Complexes of peptide and MHC class I are recognized by CD8-positive T-cells bearing the appropriate T-cell receptor (TCR), whereas complexes of peptide and MHC class II molecules are recognized by CD4-positive-helper-T-cells bearing the appropriate TCR. Since both types of response, CD8 and CD4 dependent, contribute jointly and synergistically to the anti-tumor effect, the identification and characterization of tumor-associated antigens and corresponding T cell receptors is important in the development of cancer immunotherapies such as vaccines and cell therapies.

In the MHC class I dependent immune reaction, peptides not only have to be able to bind to certain MHC class I molecules expressed by tumor cells, they subsequently also have to be recognized by T-cells bearing specific T-cell receptors (TCR). Therefore, TAAs are a starting point for the development of a T-cell based therapy including but not limited to tumor vaccines and cell therapies.

Approximately 90 percent of peripheral blood T cells express a TCR consisting of an α polypeptide and a β polypeptide. Beside αβ T cells, a small percentage of T cells (about 5% of total T cells) have been shown to express a TCR consisting of a γ polypeptide and a δ polypeptide. γδ T cells are found at their highest abundance in the gut mucosa, within a population of lymphocytes known as intraepithelial lymphocytes (IELs). The antigenic molecules that activate γδ T cells are still widely unknown. However, γδ T cells are not MHC restricted and seem to be able to recognize whole proteins rather than requiring peptides to be presented by MHC molecules on antigen presenting cells, although some recognize MHC class IB molecules. Human Vγ9/Vδ2 T cells, which constitute the major γδ T cell population in peripheral blood, are unique in that they specifically and rapidly respond to a small non-peptidic microbial metabolite, HMB-PP, an isopentenyl pyrophosphate precursor.

The chains of the T cell antigen receptor of a T cell clone are each composed of a unique combination of domains designated variable (V), [diversity (D),] joining (J), and constant (C). In each T cell clone, the combination of V, D and J domains of both the alpha and the beta chains or of both the delta and gamma chains participates in antigen recognition in a manner which is uniquely characteristic of that T cell clone and defines a unique binding site, also known as the idiotype of the T cell clone. In contrast, the C domain does not participate in antigen binding.

A TCR is a heterodimeric cell surface protein of the immunoglobulin super-family, which is associated with invariant proteins of the CD3 complex involved in mediating signal transduction. TCRs exist in αβ and γδ forms, which are structurally similar but have quite distinct anatomical locations and probably functions. The extracellular portion of native heterodimeric αβTCR and γδTCR each contain two polypeptides, each of which has a membrane-proximal constant domain, and a membrane-distal variable domain. Each of the constant and variable domains includes an intra-chain disulfide bond. The variable domains contain the highly polymorphic loops analogous to the complementarity determining regions (CDRs) of antibodies. The use of TCR gene therapy overcomes a number of current hurdles. It allows equipping patients' own T cells with desired specificities and generation of sufficient numbers of T cells in a short period of time, avoiding their exhaustion. The TCR will be transduced into central memory T cells or T cells with stem cell characteristics, which may ensure better persistence and function upon transfer. TCR-engineered T cells will be infused into cancer patients rendered lymphopenic by chemotherapy or irradiation, allowing efficient engraftment but inhibiting immune suppression.

The gene DCAF4L2 encodes for DDB1 and CUL4 associated factor 4-like 2. The specific function of this protein remains to be elucidated; nevertheless, the DCAF4L2 gene was shown to be associated with optic disc morphology and cleft lip development Springelkamp H, et al. Meta-analysis of Genome-Wide Association Studies Identifies Novel Loci Associated With Optic Disc Morphology. Genet Epidemiol. 2015 March; 39(3):207-16. Beaty T H et al. Confirming genes influencing risk to cleft lip with/without cleft palate in a case-parent trio study. Hum Genet. 2013 July; 132(7):771-81).

While advances have been made in the development of molecular-targeting drugs for cancer therapy, there remains a need in the art to develop new anti-cancer agents that specifically target molecules highly specific to cancer cells. The present description addresses that need by providing novel TCRs targeting a TAA-epitope derived from DCAF4L2, respective recombinant TCR constructs, nucleic acids, vectors and host cells that specifically bind TAA epitope(s) as disclosed; and methods of using such molecules in the treatment of cancer.

SUMMARY

The object of the invention is solved in a first aspect thereof by an antigen recognizing construct comprising at least one complementary determining region (CDR) 3 having at least 50%, 60%, 70%, 80%, 90%, 95%, 98%, 99%, or preferably 100% sequence identity to an amino acid sequence selected from SEQ ID Nos. 3, 9, 15, 21, 27 and 33.

The antigen recognizing constructs according to the present invention recognize and specifically recognize the epitope of the invention comprising or consisting of the amino acid sequence "ILQDGQFLV" (one-letter code) according to SEQ ID NO: 49, herein designated as "DCAF4L2-001" or sometimes only "peptide" or "epitope" of the invention. The peptide is preferably recognized when bound to MHC. US 2016-0280738 A1 (herewith incorporated in its entirety) discloses the DCAF4L2-001 peptide, and uses thereof).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF A PREFERRED EMBODIMENT

Figure 1:
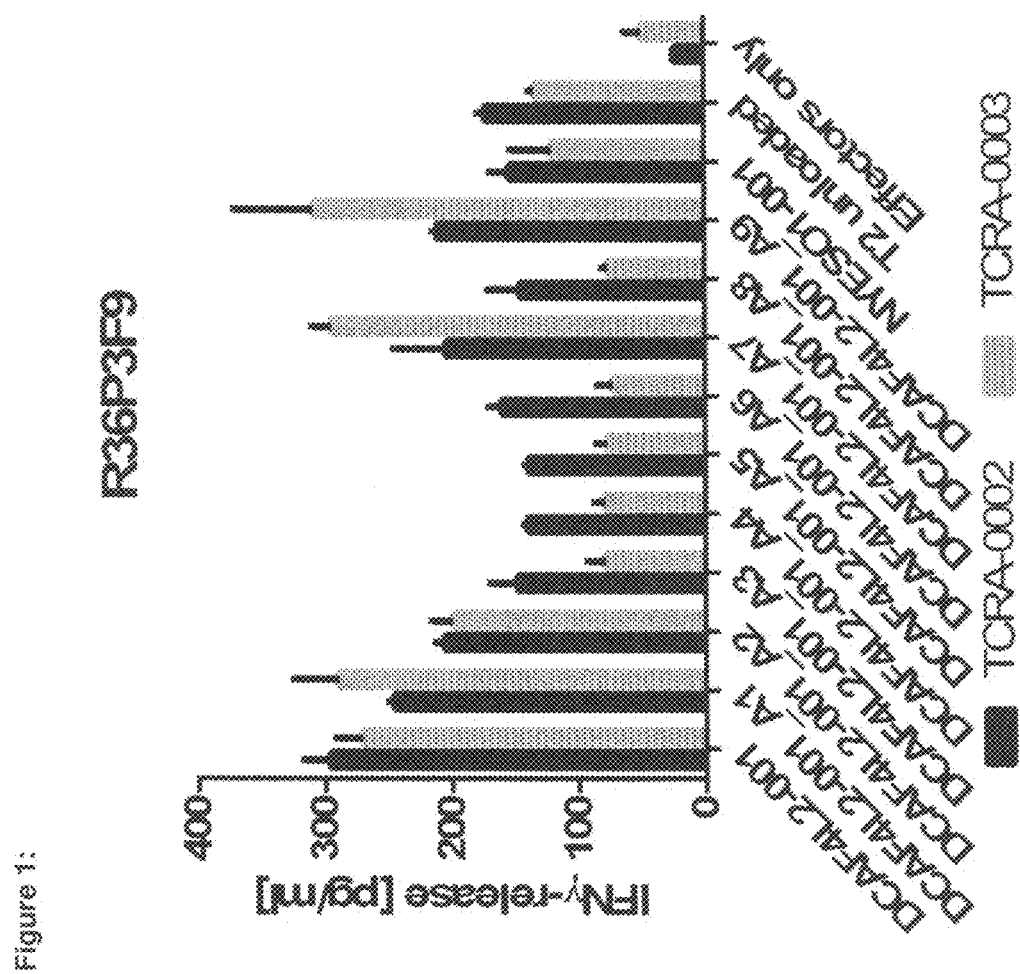
FIGS. 1-13 depict embodiments of the disclosure as disclosed herein.

In some embodiments (see also below) the antigen recognizing construct of the invention specifically binds to a TAA-peptide-HLA molecule complex, wherein the TAA peptide comprises, or alternatively consists of, a variant of the TAA which is at least 66%, preferably at least 77%, and more preferably at least 88% homologous (preferably at least 77% or at least 88% identical) to the amino acid sequence of the TAA of the invention according to SEQ ID NO: 49, wherein said variant binds to an HLA class I or class II molecule and/or induces T-cells cross-reacting with said peptide, or a pharmaceutically acceptable salt thereof, wherein said peptide is not the underlying full-length polypeptide.

As used herein, the terms "identical" or percent "identity", when used anywhere herein in the context of two or more nucleic acid or protein/polypeptide sequences, refer to two or more sequences or subsequences that are the same or have (or have at least) a specified percentage of amino acid residues or nucleotides that are the same (i.e., at, or at least, about 60% identity, preferably at, or at least, 65%, 70%, 75%, 80%, 85%, 90%, 91%, 92%, 93% or 94%, identity, and more preferably at, or at least, about 95%, 96%, 97%, 98%, 99%, or higher identity over a specified region—preferably over their full length sequences—, when compared and aligned for maximum correspondence over the comparison window or designated region) as measured using a sequence comparison algorithms, or by manual alignment and visual inspection (see, e.g., NCBI web site). In a particular embodiment, for example when comparing the protein or nucleic acid sequence of an antigen recognizing construct of the invention to another protein/gene, the percentage identity can be determined by the Blast searches supported at the Human Olfactory Data Explorer; in particular for amino acid identity, those using BLASTP 2.2.28+ with the following parameters: Matrix: BL0SUM62; Gap Penalties: Existence: 11, Extension: 1; Neighboring words threshold: 11; Window for multiple hits: 40.

In the context of the present invention it shall be understood that any embodiments referred to as "comprising" certain features of the invention, shall be understood to include in some more preferred embodiments the more restricted description of "consisting of" or "consisting essentially of" the very same features of the present invention.

In another additional or alternative embodiment, the antigen recognizing construct may further comprise a CDR1 and/or a CDR2 domain sequence. Within the variable domain, CDR1 and CDR2 are found in the variable (V) region of a polypeptide chain, and CDR3 includes some of V, all of diversity (D) and joining (J) regions. CDR3 is the most variable and is the main CDR responsible for specifically and selectively recognizing an antigen. CDR1 and CDR2 sequences may be selected from a CDR sequence of a human variable chain allele.

Native alpha-beta heterodimeric TCRs have an alpha chain and a beta chain. Each chain comprises variable, joining and constant regions, and the beta chain also usually contains a short diversity region between the variable and joining regions, but this diversity region is often considered as part of the joining region. Each variable region comprises three CDRs (Complementarity Determining Regions) embedded in a framework sequence, one being the hypervariable region named CDR3. There are several types of alpha chain variable (Va) regions and several types of beta chain variable (Vl3) regions distinguished by their framework, CDR1 and CDR2 sequences, and by a partly defined CDR3 sequence. The Va types are referred to in IMGT nomenclature by a unique TRAV number, Vl3 types are referred to by a unique TRBV number. For more information on immunoglobulin antibody and TCR genes see the international lmMunoGeneTics information System®, Lefranc M-P et al (Nucleic Acids Res. 2015 January; 43 (Database issue):0413-22).

Therefore, in one additional or alternative embodiment the antigen recognizing construct of the invention comprises CDR1, CDR2 and CDR3 sequences in a combination as provided in table 1 herein below, which display the respective variable chain allele together with the CDR3 sequence.

Therefore, preferred are antigen recognizing constructs of the invention which comprise at least one, preferably, all three CDR sequences CDR1, CDR2 and CDR3. Preferably, an antigen recognizing construct of the invention comprises the respective CDR1 to CDR3 of one individual herein disclosed TCR variable region of the invention (see table 1 herein below and the example section).

The term "specificity" or "antigen specificity" or "specific for" a given antigen, as used herein means that the antigen recognizing construct can specifically bind to said antigen, preferably a TAA antigen, more preferably with high avidity, when said antigen is presented by HLA, preferably by HLA A2. For example, a TCR, as antigen recognizing construct, may be considered to have "antigenic specificity" for the TAA, if T cells expressing the TCR secrete at least 200 pg/ml or more (e.g., 250 pg/ml or more, 300 pg/ml or more, 400 pg/ml or more, 500 pg/ml or more, 600 pg/ml or more, 700 pg/ml or more, 1000 pg ml or more, 2,000 pg/ml or more, 2,500 pg/ml or more, 5,000 pg/ml or more) of interferon γ (IFN-γ) upon co-culture with target cells pulsed with a low concentration of a TAA antigen, such as the TAA epitopes and antigens provided herein below (e.g., about 10-11 mol/l, 10-10 mol/l, 10-9 mol/l, 10-8 mol/l, 10-7 mol/l, 10-6 mol/l, 10-5 mol/l). Alternatively, or additionally, a TCR may be considered to have "antigenic specificity" for the TAA, if T cells expressing the TCR secrete at least twice as much IFN-γ as the untransduced background level of IFN-γ upon co-culture with target cells pulsed with a low concentration of the TAA antigens. Such a "specificity" as described above can—for example—be analyzed with an ELISA.

In one alternative or additional embodiment of the invention, the antigen recognizing construct selectively binds to a TAA derived antigenic peptide; preferably wherein the TAA antigenic peptide is a protein epitope or peptide having an amino acid sequence shown in SEQ ID NO: 49 or a variant thereof, wherein the variant is an amino acid deletion, addition, insertion or substitution of not more than three, preferably two and most preferably not more than one amino acid position. The antigen recognizing construct may selectively bind to modified versions (variants) of the TAA peptide DCAF4L2-001_A1 to A9 (as shown in SEQ ID NOs: 50 to 58) and DCAF4L2-001_T1 to T9 (as shown in SEQ ID NOs: 70 to 78). In contrast, the antigen recognizing construct does not bind to peptides with similar sequence to DCAF4L2-001 (as shown in SEQ ID NOs: 59 to 68).

The term "selectivity" or "selective recognizing/binding" is understood to refer to the property of an antigen recognizing construct, such as a TCR or antibody, to selectively recognize or bind to preferably only one specific epitope and preferably shows no or substantially no cross-reactivity to another epitope. Preferably "selectivity" or "selective recognizing/binding" means that the antigen recognizing construct (e.g. a TCR) selectively recognizes or binds to preferably only one specific epitope and preferably shows no or substantially no cross-reactivity to another epitope, wherein said epitope is unique for one protein, such that the antigen recognizing construct shows no or substantially no cross-reactivity to another epitope and another protein.

The antigen recognizing construct according to the invention is preferably selected from an antibody, or derivative or fragment thereof, or a T cell receptor (TCR), or derivative or fragment thereof. A derivative or fragment of an antibody or TCR of the invention shall preferably retain the antigen binding/recognizing ability of the parent molecule, in particular its specificity and/or selectivity as explained above. Such binding functionality may be retained by the presence of a CDR3 region as defined herein.

In an embodiment of the invention, the inventive TCRs are able to recognize TAA antigens in a major histocompatibility complex (MHC) class I-dependent manner. "MHC class I-dependent manner," as used herein, means that the TCR elicits an immune response upon binding to TAA antigens within the context of an MHC class I molecule. The MHC class I molecule can be any MHC class I molecule known in the art, e.g., HLA-A molecules. In a preferred embodiment of the invention, the MHC class I molecule is an HLA-A2 molecule.

The invention provides both single chain antigen recognizing construct and double chain recognizing constructs.

In an embodiment, the TCR alpha variable domain has at least one mutation relative to a TCR alpha domain shown in Table 1; and/or the TCR beta variable domain has at least one mutation relative to a TCR alpha domain shown in Table 1. In an embodiment, a TCR comprising at least one mutation in the TCR alpha variable domain and/or TCR beta variable domain has a binding affinity for, and/or a binding half-life for, an TAA peptide-HLA molecule complex, which is at least double that of a TCR comprising the unmutated TCR alpha domain and/or unmutated TCR beta variable domain.

The TCR alpha chains of the present description may further comprise a TCR alpha transmembrane domain and/or a TCR alpha intracellular domain. The TCR beta chains of the present description may further comprise a TCR beta transmembrane domain and/or a TCR beta intracellular domain.

The invention in particular provides a TCR as antigen recognizing construct, or fragment or derivative thereof. The TCR preferably is of human, which is understood as being generated from a human TCR locus and therefore comprising human TCR sequences. Furthermore, the TCR of the invention may be characterized in that it is of human origin and specifically recognizes a TAA antigen of the invention.

Another embodiment of the invention additionally or alternatively provides the antigen recognizing construct described above, which induces an immune response, preferably wherein the immune response is characterized by an increase in interferon (IFN) γ levels.

TCRs of the invention may be provided as single chain α or β, or γ and δ, molecules, or alternatively as double chain constructs composed of both the α and β chain, or γ and β chain.

The antigen recognizing construct of the invention may comprise a TCR α or γ chain; and/or a TCR β or δ chain; wherein the TCR α or γ chain comprises a CDR3 having at least 50%, 60%, 70%, 80%, 90%, 95%, 98%, 99%, or 100% sequence identity to an amino acid sequence selected from SEQ ID Nos. 3, 15, and 27, and/or wherein the TCR β or δ chain comprises a CDR3 having at least 50%, 60%, 70%, 80%, 90%, 95%, 98%, 99%, or 100% sequence identity to an amino acid sequence selected from SEQ ID Nos. 9, 21, and 33.

Most preferably, in some additional embodiments, wherein the disclosure refers to antigen recognizing constructs comprising any one, two or all of the CDR1 to CDR3 regions of the herein disclosed TCR chains (see Table 1), such antigen recognizing constructs may be preferred, which comprise the respective CDR sequence of the invention with not more than three, two, and preferably only one, modified amino acid residues. A modified amino acid residue may be selected from an amino acid insertion, deletion or substitution. Most preferred is that the three, two, preferably only one modified amino acid residue is the first or last amino acid residue of the respective CDR sequence. If the modification is a substitution then it is preferable in some embodiments that the substitution is a conservative amino acid substitution.

If the antigen recognizing construct of the invention is composed of at least two amino acid chains, such as a double chain TCR, or antigen binding fragment thereof, the antigen recognizing construct may comprises in a first polypeptide chain the amino acid sequence according to SEQ ID NO: 3, and in a second polypeptide chain the amino acid sequence according to SEQ ID NO: 9; or in a first polypeptide chain the amino acid sequence according to SEQ ID NO: 15, and in a second polypeptide chain the amino acid sequence according to SEQ ID NO: 21; or in a first polypeptide chain the amino acid sequence according to SEQ ID NO: 27, and in a second polypeptide chain the amino acid sequence according to SEQ ID NO: 33. Any one of the aforementioned double chain TCR, or antigen binding fragments thereof, are preferred TCR of the present invention. In some embodiments, the CDR3 of the double chain TCR of the invention may be mutated. Mutations of the CDR3 sequences of SEQ ID NOs: 9 to 28 as provided above preferably include a substitution, deletion, addition, or insertion of not more than three, preferably two, and most preferably not more than one amino acid residue. In some embodiments, the first polypeptide chain may be a TCR α or γ chain, and the second polypeptide chain may be a TCR β or δ chain. Preferred is the combination of an αβ or γδ TCR.

The TCR, or the antigen binding fragment thereof, is in some embodiments composed of a TCR α and a TCR β chain, or γ and δ chain. Such a double chain TCR comprises within each chain variable regions, and the variable regions each comprise one CDR1, one CDR2 and one CDR3 sequence. The TCRs comprises the CDR1 to CDR3 sequences as comprised in the variable chain amino acid sequence of SEQ ID NO: 4 and SEQ ID NO: 10 (R36P3F9), or SEQ ID NO: 16 and SEQ ID NO: 22 (R52P2G11); or SEQ ID NO: 28 and SEQ ID NO: 34 (R53P2A9).

Some embodiments of the invention pertain to a TCR, or a fragment thereof, composed of a TCR α and a TCR β chain, wherein said TCR comprises the variable region sequences having at least 50%, 60%, 70%, 80%, 90%, 95%, 98%, 99%, or preferably 100% sequence identity to the amino acid sequence selected from the α and β chain according to SEQ ID NO: 4 and 10 respectively, or 16 and 22 respectively; or 28 and 34 respectively.

The inventive TCRs may further comprise a constant region derived from any suitable species, such as any mammal, e.g., human, rat, monkey, rabbit, donkey, or mouse. In an embodiment of the invention, the inventive TCRs further comprise a human constant region. In some preferred embodiments, the constant region of the TCR of the invention may be slightly modified, for example, by the introduction of heterologous sequences, preferably mouse sequences, which may increase TCR expression and stability.

Some embodiments of the invention pertain to a TCR, or a fragment thereof, composed of a TCR α and a TCR β chain, wherein said TCR comprises the constant region having at least 50%, 60%, 70%, 80%, 90%, 95%, 98%, 99%, or preferably 100% sequence identity to an amino acid sequence selected from of the α and β chain according to SEQ ID NO: 5 and 11 respectively, or 17 and 23 respectively; or 29 and 35 respectively.

The TCR α or γ chain of the invention may further comprise a CDR1 having at least 50%, 60%, 70%, 80%, 90%, 95%, 98%, 99%, or 100% sequence identity to an amino acid sequence selected from SEQ ID Nos. 1, 13, and 25; and/or a CDR2 having at least 50%, 60%, 70%, 80%, 90%, 95%, 98%, 99%, or 100% sequence identity to an amino acid sequence selected from SEQ ID Nos. 2, 14, and 26.

According to the invention the TCR β or δ chain may further comprise a CDR1 having at least 50%, 60%, 70%, 80%, 90%, 95%, 98%, 99%, or 100% sequence identity to an amino acid sequence selected from SEQ ID Nos. 7, 19, and 31; and/or a CDR2 having at least 50%, 60%, 70%, 80%, 90%, 95%, 98%, 99%, or 100% sequence identity to an amino acid sequence selected from SEQ ID Nos. 8, 20, and 32.

The antigen recognizing construct may in a further embodiment comprise a binding fragment of a TCR, and wherein said binding fragment comprises CDR1 to CDR3, optionally selected from the CDR1 to CDR3 sequences having the amino acid sequences of SEQ ID Nos. 1, 2, 3, or 7, 8, 9 or 13, 14, 15, or 19, 20, 21, or 25, 26, 27 or 31, 32, 33.

In further embodiments of the invention the antigen recognizing construct as described herein elsewhere is a TCR, or a fragment thereof, composed of at least one TCR α and one TCR β chain sequence, wherein said TCR α chain sequence comprises the CDR1 to CDR3 sequences having the amino acid sequences of SEQ ID NO: 1 to 3, and said TCR β chain sequence comprises the CDR1 to CDR3 sequences having the amino acid sequences of SEQ ID NO: 7 to 9; or wherein said TCR α chain sequence comprises the CDR1 to CDR3 sequences having the amino acid sequences of SEQ ID NO: 13 to 15, and said TCR β chain sequence comprises the CDR1 to CDR3 sequences having the amino acid sequences of SEQ ID NO: 19 to 21; or wherein said TCR α chain sequence comprises the CDR1 to CDR3 sequences having the amino acid sequences of SEQ ID NO: 25 to 27, and said TCR β chain sequence comprises the CDR1 to CDR3 sequences having the amino acid sequences of SEQ ID NO: 31 to 33.

In further embodiments of the invention the antigen recognizing construct as described herein before is a TCR, or a fragment thereof, comprising at least one TCR α and one TCR β chain sequence, wherein said TCR α chain sequence comprises a variable region sequence having the amino acid sequence of SEQ ID No. 4, and wherein said TCR β chain sequence comprises a variable region sequence having the amino acid sequence of SEQ ID No. 10; or wherein said TCR α chain sequence comprises a variable region sequence having the amino acid sequence of SEQ ID No. 16, and wherein said TCR β chain sequence comprises a variable region sequence having the amino acid sequence of SEQ ID No. 22; or wherein said TCR α chain sequence comprises a variable region sequence having the amino acid sequence of SEQ ID No. 28, and wherein said TCR β chain sequence comprises a variable region sequence having the amino acid sequence of SEQ ID No. 34.

In further embodiments of the invention the antigen recognizing construct as described herein before is a TCR, or a fragment thereof, further comprising a TCR constant region having at least 50%, 60%, 70%, 80%, 90%, 95%, 98%, 99%, or 100% sequence identity to an amino acid sequence selected from SEQ ID Nos. 5, 11, 17, 23, 29 and 35, preferably wherein the TCR is composed of at least one TCR α and one TCR β chain sequence, wherein the TCR α chain sequence comprises a constant region having at least 50%, 60%, 70%, 80%, 90%, 95%, 98%, 99%, or 100% sequence identity to an amino acid sequence selected from SEQ ID Nos. 5, 17, and 29.

Also disclosed are antigen recognizing constructs as described herein before comprising a first TCR chain having at least 50%, 60%, 70%, 80%, 90%, 95%, 98%, 99%, or 100% sequence identity to the amino acid sequence of SEQ ID No. 6, and a second TCR chain having at least 50%, 60%, 70%, 80%, 90%, 95%, 98%, 99%, or 100% sequence identity to the amino acid sequence of SEQ ID No. 12. The invention also provides TCRs comprising a first TCR chain having at least 50%, 60%, 70%, 80%, 90%, 95%, 98%, 99%, or 100% sequence identity to the amino acid sequence of SEQ ID No. 18, and a second TCR chain having at least 50%, 60%, 70%, 80%, 90%, 95%, 98%, 99%, or 100% sequence identity to the amino acid sequence of SEQ ID No. 24. In further embodiments the invention provides antigen recognizing constructs which are TCR and comprise a first TCR chain having at least 50%, 60%, 70%, 80%, 90%, 95%, 98%, 99%, or 100% sequence identity to the amino acid sequence of SEQ ID No. 30, and a second TCR chain having at least 50%, 60%, 70%, 80%, 90%, 95%, 98%, 99%, or 100% sequence identity to the amino acid sequence of SEQ ID No. 36.

As used herein, the term "murine" or "human," when referring to an antigen recognizing construct, or a TCR, or any component of a TCR described herein (e.g., complementarity determining region (CDR), variable region, constant region, α chain, and/or β chain), means a TCR (or component thereof), which is derived from a mouse or a human unrearranged TCR locus, respectively.

In an embodiment of the invention, chimeric TCR are provided, wherein the TCR chains comprise sequences from multiple species. Preferably, a TCR of the invention may comprise an α chain comprising a human variable region of an α chain and, for example, a murine constant region of a murine TCR α chain.

In one embodiment, the TCR of the invention is a human TCR comprising human variable regions according to the above embodiments and human constant regions.

In some embodiments the antigen recognizing construct is murinized or humanized. These terms are used when amino acid sequences from a foreign species are introduced into a construct of the invention. Murinization may replace the human TCRalpha and TCRbeta constant regions by their murine counterparts or may introduce essential murine (amino acid) residues into the sequence that mediate an enhanced functional effect. In humanized sequences the murine sequence is modified by introducing human counterparts or residues.

The TCR of the invention may be modified in order to avoid mispairing of the TCR chains. The term "mispairing" shall relate to the incorrect pairing between a TCR chain of a TCR α/γ or β/δ transgene of the invention and an endogenous TCR α/γ or β/δ chain, respectively, and results in diluted cell surface expression of the transgenic TCRαβ/γδ heterodimer, which reduces the functional avidity of the modified T cells. Preferably, Q at position 44 in the TCR variable domain according to the IMGT numbering is substituted by another amino acid in one or both chains of the TCR of the invention. The substitution is preferably selected from the group consisting of R, D, E, K, I, W and V.

The TCR of the invention may be provided as a single chain TCR (scTCR). A scTCR can comprise a polypeptide of a variable region of a first TCR chain (e.g., an alpha chain) and a polypeptide of an entire (full-length) second TCR chain (e.g., a beta chain), or vice versa. Furthermore, the scTCR can optionally comprise one or more linkers which join the two or more polypeptides together. The linker can be, for instance, a peptide, which joins together two single chains, as described herein. Also provided is such a scTCR of the invention, which is fused to a human cytokine, such as IL-2, IL-7 or IL-15.

The antigen recognizing construct according to the invention can also be provided in the form of a multimeric complex, comprising at least two scTCR molecules, wherein said scTCR molecules are each fused to at least one biotin moiety, or other interconnecting molecule/linker, and wherein said scTCRs are interconnected by biotin-streptavidin interaction to allow the formation of said multimeric complex. Similar approaches known in the art for the generation of multimeric TCR are also possible and included in this disclosure. Also provided are multimeric complexes of a higher order, comprising more than two scTCR of the invention.

For the purposes of the present invention, a TCR is a moiety having at least one TCR alpha or gamma and/or TCR beta or delta variable domain. Generally, they comprise both a TCR alpha variable domain and a TCR beta variable domain, alternatively both a TCR gamma variable domain and a TCR delta variable domain. They may be αβ/γδ heterodimers or may be in single chain format. For use in adoptive therapy, an αβ or γδ heterodimeric TCR may, for example, be transfected as full length chains having both cytoplasmic and transmembrane domains. If desired, an introduced disulfide bond between residues of the respective constant domains may be present.

In a preferred embodiment, the antigen recognizing construct is a human TCR, or fragment or derivative thereof. A human TCR or fragment or derivative thereof is a TCR, which comprises over 50% of the corresponding human TCR sequence. Preferably, only a small part of the TCR sequence is of artificial origin or derived from other species. It is known, however, that chimeric TCRs, e.g. derived from human origin with murine sequences in the constant domains, are advantageous. Particularly preferred are, therefore, TCRs in accordance with the present invention, which contains murine sequences in the extracellular part of their constant domains.

Thus, it is also preferred that the inventive antigen recognizing construct is able to recognize its antigen in a human leucocyte antigen (HLA) dependent manner, preferably in a HLA-A02 dependent manner. The term "HLA dependent manner" in the context of the present invention means that the antigen recognizing construct binds to the antigen only in the event that the antigenic peptide is presented by said HLA.

The antigen recognizing construct in accordance with the invention in one embodiment preferably induces an immune response, preferably wherein the immune response is characterized by the increase in interferon (IFN) γ levels.

Also provided by the invention is a polypeptide comprising a functional portion of any of the TCRs (or functional variants thereof) described herein, for examples, of any one of the TCRs selected from R36P3F9, R52P2G11 and R53P2A9, as provided in the example section and table 1. The term "polypeptide" as used herein includes oligopeptides and refers to a single chain of amino acids connected by one or more peptide bonds. With respect to the inventive polypeptides, the functional portion can be any portion comprising contiguous amino acids of the TCR (or functional variant thereof), of which it is a part, provided that the functional portion specifically binds to the TAA antigen derived peptide DCAF4L2-001 (SEQ ID NOs: 49, and variants in SEQ ID NOs: 50 to 58). The term "functional portion" when used in reference to a TCR (or functional variant thereof) refers to any part or fragment of the TCR (or functional variant thereof) of the invention, which part or fragment retains the biological activity of the TCR (or functional variant thereof), of which it is a part (the parent TCR or parent functional variant thereof). Functional portions encompass, for example, those parts of a TCR (or functional variant thereof) that retain the ability to specifically bind to the TAA antigen (in an HLA dependent manner), or detect, treat, or prevent cancer, to a similar extent, the same extent, or to a higher extent, as the parent TCR (or functional variant thereof). In reference to the parent TCR (or functional variant thereof), the functional portion can comprise, for instance, about 10%, 25%, 30%, 50%, 68%, 80%, 90%, 95%, or more, of the parent TCR variable sequences (or functional variant thereof).

The functional portion can comprise additional amino acids at the amino or carboxy terminus of the portion, or at both termini, in which additional amino acids are not found in the amino acid sequence of the parent TCR or functional variant thereof. Desirably, the additional amino acids do not interfere with the biological function of the functional portion, e.g., specifically binding to the TAA antigens; and/or having the ability to detect cancer, treat or prevent cancer, etc. More desirably, the additional amino acids enhance the biological activity, as compared to the biological activity of the parent TCR or functional variant thereof.

The polypeptide can comprise a functional portion of either or both of the α and β chains of the TCRs or functional variant thereof of the invention, such as a functional portion comprising one of more of CDR1, CDR2, and (preferably) CDR3 of the variable region(s) of the α chain and/or β chain of a TCR or functional variant thereof of the invention. In an embodiment of the invention, the polypeptide can comprise a functional portion comprising the amino acid sequence of SEQ ID NO: 3, 9, 15, 21, 27, and 33 (CDR3 of the variable regions of the TCR of the invention), or a combination thereof. In an embodiment of the invention, the inventive polypeptide can comprise, for instance, the variable region of the inventive TCR or functional variant thereof comprising a combination of the CDR regions set forth above. In this regard, the polypeptide can comprise the amino acid sequence of any of SEQ ID NO: 4, 10, 16, 22, 28, and 34 (the variable regions of an α or β chain of the TCR of the invention).

In some instances, the construct of the invention may comprise one or two polypeptide chains comprising a sequence according to any of the SEQ ID NO: 1 to 36 (CDR sequences, constant and variable regions and full length sequences), or functional fragments thereof, and further comprise(s) other amino acid sequences, e.g., an amino acid sequence encoding an immunoglobulin or a portion thereof, then the inventive protein can be a fusion protein. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide may include any peptidic or proteinaceous molecule, or a portion thereof, including, but not limited to an immunoglobulin, CD3, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods. In some embodiments of the invention, the TCRs (and functional portions and functional variants thereof), polypeptides, and proteins of the invention may be expressed as a single protein comprising a linker peptide linking the α chain and the β chain, and linking the γ chain and the δ chain. In this regard, the TCRs (and functional variants and functional portions thereof), polypeptides, and proteins of the invention comprising the amino acid sequences of the variable regions of the TCR of the invention and may further comprise a linker peptide. The linker peptide may advantageously facilitate the expression of a recombinant TCR (including functional portions and functional variants thereof), polypeptide, and/or protein in a host cell. The linker peptide may comprise any suitable amino acid sequence. Linker sequences for single chain TCR constructs are well known in the art. Such a single chain construct may further comprise one, or two, constant domain sequences. Upon expression of the construct including the linker peptide by a host cell, the linker peptide may also be cleaved, resulting in separated α and β chains, and separated γ and δ chain.

As already mentioned above, the binding functionality of the TCR of the invention may be provided in the framework of an antibody. For example, CDR sequences of the TCR of the invention, possibly including additional 3, 2 or 1 N and/or C terminal framework residues, may be directly grafted into an antibody variable heavy/light chain sequence. The term "antibody" in its various grammatical forms is used herein to refer to immunoglobulin molecules and immunologically active portions of immunoglobulin molecules, i.e., molecules that contain an antigen-binding site or a paratope. Such molecules are also referred to as "antigen binding fragments" of immunoglobulin molecules. The invention further provides an antibody, or antigen binding portion thereof, which specifically binds to the antigens described herein. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form.

The term "antibody" includes, but is not limited to, genetically engineered or otherwise modified forms of immunoglobulins, such as intrabodies, chimeric antibodies, fully human antibodies, humanized antibodies (e.g. generated by "CDR-grafting"), antibody fragments, and heteroconjugate antibodies (e.g., bispecific antibodies, diabodies, triabodies, tetra-bodies, etc.). The term "antibody" includes cys-diabodies and minibodies. Thus, each and every embodiment provided herein in regard to "antibodies", or "antibody like constructs" is also envisioned as, bi-specific antibodies, diabodies, scFv fragments, chimeric antibody receptor (CAR) constructs, diabody and/or minibody embodiments, unless explicitly denoted otherwise. The term "antibody" includes a polypeptide of the immunoglobulin family or a polypeptide comprising fragments of an immunoglobulin that is capable of non-covalently, reversibly, and in a specific manner binding a corresponding antigen, preferably the TAA of the invention, as disclosed herein. An exemplary antibody structural unit comprises a tetramer. In some embodiments, a full length antibody can be composed of two identical pairs of polypeptide chains, each pair having one "light" and one "heavy" chain (connected through a disulfide bond). Antibody structure and isotypes are well known to the skilled artisan (for example from Janeway's Immunobiology, 9th edition, 2016).

The recognized immunoglobulin genes of mammals include the kappa, lambda, alpha, gamma, delta, epsilon, and mu constant region genes, as well as the myriad immunoglobulin variable region genes (for more information on immunoglobulin genes see the international lm-MunoGeneTics information System®, Lefranc M-P et al, Nucleic Acids Res. 2015 January; 43 (Database issue): 0413-22). For full-length chains, the light chains are classified as either kappa or lambda. For full-length chains, the heavy chains are classified as gamma, mu, alpha, delta, or epsilon, which in turn define the immunoglobulin classes, lgG, lgM, lgA, lgD, and lgE, respectively. The Nterminus of each chain defines a variable region of about 100 to 110 or more amino acids primarily responsible for antigen recognition. The terms variable light chain (VL) and variable heavy chain (VH) refer to these regions of light and heavy chains respectively. As used in this invention, an "antibody" encompasses all variations of antibody and fragments thereof. Thus, within the scope of this concept are full length antibodies, chimeric antibodies, humanized antibodies, single chain antibodies (scFv), Fab, Fab', and multimeric versions of these fragments (e.g., F(ab')2) with the same, essentially the same or similar binding specificity. In some embodiments, the anti-body binds specifically to a peptide TAA of the invention. Preferred antigen recognizing constructs according to the invention include an antibody heavy chain, preferably the variable domain thereof, or an antigen binding fragment thereof, and/or an antibody light chain, preferably the variable domain thereof, or an antigen binding fragment thereof. Similarly, disulfide-stabilized variable region fragments (dsFv) can be prepared by recombinant DNA technology, antibody fragments of the invention, however, are not limited to these exemplary types of antibody fragments. Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles). In some instances, the TCR CDR3 sequence may be slightly modified, but preferably by not more than 3 amino acid residues, preferably only two and most preferably only one amino acid position, as compared to the CDR3 sequences provided in SEQ ID Nos: 3, 9, 15, 21, 27, and 33. Preferably, the antibodies comprise the CDR3, preferably all of CDR1 to CDR3 regions in the combination, as indicated for the TCR of the invention in table 1, in each case independently, optionally with not more than three or two, preferably one, amino acid substitution(s), insertion(s) and/or deletion(s) compared to these sequences.

Suitable methods of making antibodies are known in the art. For instance, standard hybridoma methods are described in, e.g., Kohler and Milstein, Eur. J. Immunol, 5, 51 1-519 (1976), Harlow and Lane (eds.), Antibodies: A Laboratory Manual, CSH Press (1988), and C. A. Janeway et al. (eds.), Immunobiology, 8 Ed., Garland Publishing, New York, N.Y. (2011)). Alternatively, other methods, such as EBV-hybridoma methods (Haskard and Archer, J. Immunol. Methods, 74(2), 361-67 (1984), and Roder et al, Methods Enzymol, 121, 140-67 (1986)), and bacteriophage vector expression systems (see, e.g., Huse et al., Science, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266.

Some embodiments of the invention also pertain to TCRs, or functional fragments and polypeptides thereof, which are soluble TCRs. As used herein, the term "soluble T-cell receptor" refers to heterodimeric truncated variants of native TCRs, which comprise extracellular portions of the TCR α-chain and β-chain, for example linked by a disulfide bond, but which lack the transmembrane and cytosolic domains of the native protein. The terms "soluble T-cell receptor α-chain sequence and soluble T-cell receptor β-chain sequence" refer to TCR α-chain and β-chain sequences that lack the transmembrane and cytosolic domains. The sequence (amino acid or nucleic acid) of the soluble TCR α-chain and β-chains may be identical to the corresponding sequences in a native TCR or may comprise variant soluble TCR α-chain and β-chain sequences, as compared to the corresponding native TCR sequences. The term "soluble T-cell receptor" as used herein encompasses soluble TCRs with variant or non-variant soluble TCR α-chain and β-chain sequences. The variations may be in the variable or constant regions of the soluble TCR α-chain and β-chain sequences and can include, but are not limited to, amino acid deletion, insertion, substitution mutations as well as changes to the nucleic acid sequence, which do not alter the amino acid sequence. Soluble TCR of the invention in any case retain the binding functionality of their parent molecules.

The above problem is further solved by a nucleic acid encoding for an antigen recognizing construct of the invention, or any of the aforementioned protein or polypeptide constructs. The nucleic acid preferably (a) has a strand encoding for an antigen recognizing construct according to the invention; (b) has a strand complementary to the strand in (a); or (c) has a strand that hybridizes under stringent conditions with a molecule as described in (a) or (b). Stringent conditions are known to the person of skill in the art, specifically from Sambrook et al, "Molecular Cloning". In addition to that, the nucleic acid optionally has further sequences, which are necessary for expressing the nucleic acid sequence corresponding to the protein, specifically for expression in a mammalian/human cell. The nucleic acid used can be contained in a vector suitable for allowing expression of the nucleic acid sequence corresponding to the peptide in a cell. However, the nucleic acids can also be used to transform an antigen-presenting cell, which may not be restricted to classical antigen-presenting cells, such as dendritic cells, in such a way that they themselves produce the corresponding proteins on their cellular surface.

In some embodiments, the polypeptides of the antigen recognizing constructs can be encoded by nucleic acids and expressed in vivo or in vitro. Thus, in some embodiments, a nucleic acid encoding an antigen recognizing construct is provided. In some embodiments, the nucleic acid encodes one part or monomer of an antigen recognizing construct of the invention (for example one of two chains of a TCR of the invention), and/or another nucleic acid encodes another part or monomer of an antigen recognizing construct of the invention (for example the other of two chains of the TCR). In some embodiments, the nucleic acid encodes two or more antigen recognizing construct polypeptide chains, for example, at least 2 TCR chains. Nucleic acids encoding multiple antigen recognizing construct chains can include nucleic acid cleavage sites between at least two chain sequences, can encode transcription or translation start site between two or more chains sequences, and/or can encode proteolytic target sites between two or more antigen recognizing construct chains.

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and can contain a natural, non-natural or altered internucleotide linkage, such as a phosphoroamidate linkage or a phosphorothioate linkage, instead of the phosphodiester found between the nucleotides of an unmodified oligonucleotide.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication. The nucleic acid can comprise any nucleotide sequence, which encodes any of the TCRs, polypeptides, or proteins, or functional portions or functional variants thereof described herein.

Furthermore, the invention provides a vector comprising a nucleic acid in accordance to the invention as described above. Desirably, the vector is an expression vector or a recombinant expression vector. The term "recombinant expression vector" refers in context of the present invention to a nucleic acid construct that allows for the expression of an mRNA, protein or polypeptide in a suitable host cell. The recombinant expression vector of the invention can be any suitable recombinant expression vector, and can be used to transform or transfect any suitable host. Suitable vectors include those designed for propagation and expansion or for expression or both, such as plasmids and viruses. Examples of animal expression vectors include pEUK-CI, pMAM, and pMAMneo. Preferably, the recombinant expression vector is a viral vector, e.g., a retroviral vector. The recombinant expression vector comprises regulatory sequences, such as transcription and translation initiation and termination codons, which are specific to the type of host cell (e.g., bacterium, fungus, plant, or animal), into which the vector is to be introduced and in which the expression of the nucleic acid of the invention may be performed. Furthermore, the vector of the invention may include one or more marker genes, which allow for selection of transformed or transfected hosts. The recombinant expression vector can comprise a native or normative promoter operably linked to the nucleotide sequence encoding the constructs of the invention, or to the nucleotide sequence, which is complementary to or which hybridizes to the nucleotide sequence encoding the constructs of the invention. The selections of promoters include, e.g., strong, weak, inducible, tissue-specific and developmental-specific promoters. The promoter can be a non-viral promoter or a viral promoter. The inventive recombinant expression vectors can be designed for either transient expression, for stable expression, or for both. Also, the recombinant expression vectors can be made for constitutive expression or for inducible expression.

The invention also pertains to a host cell comprising an antigen recognizing construct in accordance with the invention. Specifically, the host cell of the invention comprises a nucleic acid, or a vector as described herein above. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood leukocyte (PBL) or a peripheral blood mononuclear cell (PBMC). More preferably, the host cell is a T cell. The T cell can be any T cell, such as a cultured T cell, e.g., a primary T cell, or a T cell from a cultured T cell line, e.g., Jurkat, SupT1, etc., or a T cell obtained from a mammal, preferably a T cell or T cell precursor from a human patient. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. More preferably, the T cell is a T cell isolated from a human. The T cell can be any type of T cell and can be of any developmental stage, including but not limited to, CD4-positive and/or CD8-positive, CD4-positive helper T cells, e.g., Th1 and Th2 cells, CD8-positive T cells (e.g., cytotoxic T cells), tumor infiltrating cells (TILs), memory T cells, naive T cells, and the like. Preferably, the T cell is a CD8-positive T cell or a CD4-positive T cell.

Preferably, the host cell of the invention is a lymphocyte, preferably, a T lymphocyte, such as a CD4-positive or CD8-positive T-cell. The host cell furthermore preferably is a tumor reactive T cell specific for TAA expressing tumor cells.

The object of the invention is also solved by a method of manufacturing a TAA specific antigen recognizing construct, or of a TAA specific antigen recognizing construct expressing cell line, comprising
a) Providing a suitable host cell,
b) Providing a genetic construct comprising a coding sequence encoding for an antigen recognizing construct according to the herein disclosed invention,
c) Introducing into said suitable host cell said genetic construct, and
d) Expressing said genetic construct by said suitable host cell.

The method may further comprise a step of cell surface presentation of said antigen recognizing construct on said suitable host cell.

In other preferred embodiments, the genetic construct is an expression construct comprising a promoter sequence operably linked to said coding sequence.

Preferably, said antigen recognizing construct is of mammalian origin, preferably of human origin. The preferred suitable host cell for use in the method of the invention is a mammalian cell, such as a human cell, in particular a human T lymphocyte. T cells for use in the invention are described in detail herein above.

Also encompassed by the invention are embodiments, wherein said antigen recognizing construct is a modified TCR, wherein said modification is the addition of functional domains, such as a label or a therapeutically active substance. Furthermore, encompassed are TCR having alternative domains, such as an alternative membrane anchor domain instead of the endogenous transmembrane region.

Desirably, the transfection system for introducing the genetic construct into said suitable host cell is a retroviral vector system. Such systems are well known to the skilled artisan.

Also comprised by the present invention is in one embodiment the additional method step of isolation and purification of the antigen recognizing construct from the cell and, optionally, the reconstitution of the translated antigen recognizing construct-fragments in a T-cell.

In an alternative aspect of the invention a T-cell is provided obtained or obtainable by a method for the production of a T cell receptor (TCR), which is specific for tumorous cells and has high avidity as described herein above. Such a T cell is depending on the host cell used in the method of the invention, for example, a human or non-human T-cell, preferably a human TCR.

The term "isolated" as used herein in the context of a polypeptide, such as an antigen recognizing construct (an example of which could be an antibody), refers to a polypeptide that is purified from proteins or polypeptides or other contaminants that would interfere with its therapeutic, diagnostic, prophylactic, research or other use. An antigen recognizing construct according to the invention may be a recombinant, synthetic or modified (non-natural) antigen binding construct. The term "isolated" as used herein in the context of a nucleic acid or cells refers to a nucleic acid or cells that is/are purified from DNA, RNA, proteins or polypeptides or other contaminants (such as other cells) that would interfere with its therapeutic, diagnostic, prophylactic, research or other use, or it refers to a recombinant, synthetic or modified (non-natural) nucleic acid. In this context, a "recombinant" protein/polypeptide or nucleic acid is one made using recombinant techniques. Methods and techniques for the production of recombinant nucleic acids and proteins are well known in the art.

One further aspect of the present invention relates to the herein disclosed antigen recognizing constructs, nucleic acids, vectors, pharmaceutical compositions and/or host cell for use in medicine. The use in medicine in one preferred embodiment includes the use in the diagnosis, prevention and/or treatment of a tumor disease, such as a malignant or benign tumor disease. The tumor disease is, for example, a tumor disease characterized by the expression of the TAA, in a cancer or tumor cell of said tumor disease.

With respect to the above mentioned medical applications of the antigen recognizing constructs and other materials derived therefrom, pertaining thereto or encoding the same, in accordance of the present disclosure, the to be treated and/or to be diagnosed diseases can be any proliferative disorder, preferably characterized by the expression of the TAA or TAA epitope sequence of the invention, for example any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, chronic lymphocytic leukemia, chronic myeloid cancer, colon cancer, esophageal cancer, cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, and urinary bladder cancer. A preferred cancer is cancer is cancer of the uterine cervix, oropharynx, anus, anal canal, anorectum, vagina, vulva, or penis. A particularly preferred cancer is a TAA positive (i.e. DCAF4L2-001-peptide presenting) cancer, including preferably gastrointestinal and gastric cancer.

The constructs, proteins, TCRs antibodies, polypeptides and nucleic acids of the invention are in particular for use in immune therapy, preferably, in adoptive T cell therapy. The administration of the compounds of the invention can, for example, involve the infusion of T cells of the invention into said patient. Preferably, such T cells are autologous T cells of the patient and in vitro transduced with a nucleic acid or antigen recognizing construct of the present invention.

The inventive antigen recognizing constructs, TCRs, polypeptides, proteins (including functional variants thereof), nucleic acids, recombinant expression vectors, host cells (including populations thereof), and antibodies (including antigen binding portions thereof), all of which are collectively referred to as "inventive TCR materials" hereinafter, can be formulated into a composition, such as a pharmaceutical composition. In this regard, the invention provides a pharmaceutical composition comprising any of the antigen recognizing constructs, TCRs, polypeptides, proteins, functional portions, functional variants, nucleic acids, expression vectors, host cells (including populations thereof), and antibodies (including antigen binding portions thereof) described herein, and a pharmaceutically acceptable carrier, excipient and/or stabilizer. The inventive pharmaceutical compositions containing any of the inventive TCR materials can comprise more than one inventive TCR material, e.g., a polypeptide and a nucleic acid, or two or more different TCRs (including functional portions and functional variants thereof). Alternatively, the pharmaceutical composition can comprise an inventive TCR material in combination with another pharmaceutically active agent(s) or drug(s), such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. Preferably, the carrier is a pharmaceutically acceptable carrier. With respect to pharmaceutical compositions, the carrier can be any of those conventionally used for the particular inventive TCR material under consideration. Such pharmaceutically acceptable carriers are well-known to those skilled in the art and are readily available to the public. It is preferred that the pharmaceutically acceptable carrier be one, which has no detrimental side effects or toxicity under the conditions of use.

Thus also provided is a pharmaceutical composition, comprising any of the herein described products of the invention and TCR materials of the invention, specifically any proteins, nucleic acids or host cells. In a preferred embodiment the pharmaceutical composition is for immune therapy, preferably adoptive cell therapy.

Preferably, the inventive TCR material is administered by injection, e.g., intravenously. When the inventive TCR material is a host cell expressing the inventive TCR (or functional variant thereof), the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, Ill.), PLASMA-LYTE A (Baxter, Deerfield, Ill.), about 5% dextrose in water, or Ringer's lactate. In an embodiment, the pharmaceutically acceptable carrier is supplemented with human serum albumen.

For purposes of the invention, the amount or dose (e.g., numbers of cells when the inventive TCR material is one or more cells) of the inventive TCR material administered may be sufficient to affect, e.g., a therapeutic or prophylactic response, in the subject or animal over a reasonable time frame. For example, the dose of the inventive TCR material should be sufficient to bind to a cancer antigen, or detect, treat or prevent cancer in a period of from about 2 hours or longer, e.g., 12 to 24 or more hours, from the time of administration. In certain embodiments, the time period could be even longer. The dose will be determined by the efficacy of the particular inventive TCR material and the condition of the animal (e.g., human), as well as the body weight of the animal (e.g., human) to be treated.

It is contemplated that the inventive pharmaceutical compositions, antigen recognizing constructs, TCRs (including functional variants thereof), polypeptides, proteins, nucleic acids, recombinant expression vectors, host cells, or populations of cells can be used in methods of treating or preventing cancer, or TAA-positive premalignancy. The inventive TCRs (and functional variants thereof) are believed to bind specifically to the TAA of the invention, such that the TCR (or related inventive polypeptide or protein and functional variants thereof), when expressed by or on a cell, such as a T cell, is able to mediate an immune response against a target cell expressing the TAA of the invention, preferably presenting TAA peptides via MHC I or II on the surface of said target cell. In this regard, the invention provides a method of treating or preventing a condition, in particular cancer, in a mammal, comprising administering to the mammal any of the pharmaceutical compositions, antigen recognizing constructs, in particular TCRs (and functional variants thereof), polypeptides, or proteins described herein, any nucleic acid or recombinant expression vector comprising a nucleotide sequence encoding any of the TCRs (and functional variants thereof), polypeptides, proteins described herein, or any host cell or population of cells comprising a nucleic acid or recombinant vector, which encodes any of the constructs of the invention (and functional variants thereof), polypeptides, or proteins described herein, in an amount effective to treat or prevent the condition in the mammal, wherein the condition is preferably cancer, such as a cancer expressing the TAA of the invention.

Examples of pharmaceutically acceptable carriers or diluents useful in the present invention include stabilizers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer).

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of a condition in a mammal. Furthermore, the treatment or prevention provided by the inventive method can include treatment or prevention of one or more conditions or symptoms of the condition, e.g., cancer, being treated or prevented. For example, treatment or prevention can include promoting the regression of a tumor. Also, for purposes herein, "prevention" can encompass delaying the onset of the condition, or a symptom or condition thereof.

The present invention also relates to a method of treating cancer comprising administering a TCR, a nucleic acid, or a host cell of the present description in combination with at least one chemotherapeutic agent and/or radiation therapy.

Another aspect of the invention further pertains to a method for detecting a TAA protein, or a complex of MHC and the TAA protein (protein epitope of the TAA), in a (biological) sample—such as one obtained from a subject or patient—comprising contacting the sample with an antigen recognizing construct specifically binding to said TAA peptide, or to the TAA peptide/MHC complex, and detecting the binding between said antigen recognizing construct and said TAA peptide, or to the TAA peptide/MHC complex. In some embodiments, the antigen recognizing construct is a TCR or antibody, or similar constructs, or preferably the antigen recognizing construct according to the herein described invention. In some embodiments, the (biological) sample is a sample of a tumour or a cancer (such as one of those described elsewhere herein) for example a sample comprising tumour or cancer cells.

Also provided is a method of treating cancer in a subject in need thereof, comprising:
a) isolating a cell from said subject;
b) transforming the cell with at least one vector encoding an antigen recognizing construct of the present invention to produce a transformed cell;
c) expanding the transformed cell to produce a plurality of transformed cells; and
d) administering the plurality of transformed cells to said subject.

Also provided is a method of treating cancer in a subject in need thereof, comprising:
a) isolating a cell from a healthy donor;
b) transforming the cell with a vector encoding an antigen recognizing construct of the present invention to produce a transformed cell;
c) expanding the transformed cell to produce a plurality of transformed cells; and
d) administering the plurality of transformed cells to said subject.

Also provided is a method of treating cancer in a subject in need thereof, wherein the TCR of any of the description, the nucleic acid of the description, the expression vector of the description, the host cell of the description or the pharmaceutical composition of the description is administered in at least two administrations separated by at least 24 hours.

Also provided is a method of treating cancer in a subject in need thereof, wherein the TCR of any of the description, the nucleic acid of the description, the expression vector of the description, the host cell of the description or the pharmaceutical composition of the description is administered to the subject over a period of days, weeks or months.

Also provided is a method of treating cancer in a subject in need thereof, wherein the TCR of any of the description, the nucleic acid of the description, the expression vector of the description, the host cell of the description or the pharmaceutical composition of the description is administered by local infusion. Preferably, the local infusion is administered by an infusion pump and/or a catheter system. More preferably, said local infusion is into a solid tumor, a blood vessel that feeds a solid tumor, and/or the area surrounding a solid tumor.

Also provided is a method of treating cancer in a subject in need thereof, wherein the TCR of the description, the nucleic acid of the description, the expression vector of the description, the host cell of the description or the pharmaceutical composition of the description is administered in a dose of about $10^4$ to about $10^{10}$ cells per dose.

Also provided is a method of detecting cancer in a biological sample comprising:
a) contacting the biological sample with an antigen recognizing construct (e.g. TCT) of the present description;
b) detecting binding of the antigen recognizing construct (e.g. TCR) to the biological sample.

In some embodiments, the method of detecting cancer is carried out in vitro, in vivo or in situ.

Also provided is a method of detecting the presence of a condition in a mammal. The method comprises (i) contacting a sample comprising one or more cells from the mammal with any of the inventive TCRs (and functional variants thereof), polypeptides, proteins, nucleic acids, recombinant expression vectors, host cells, populations of cells, antibodies, or antigen binding portions thereof, or pharmaceutical compositions described herein, thereby forming a complex, and detecting the complex, wherein detection of the complex is indicative of the presence of the condition in the mammal, wherein the condition is cancer, such as a TAA expressing malignancy.

With respect to the inventive method of detecting a condition in a mammal, the sample of cells can be a sample comprising whole cells, lysates thereof, or a fraction of the whole cell lysates, e.g., a nuclear or cytoplasmic fraction, a whole protein fraction, or a nucleic acid fraction.

For purposes of the inventive detecting method, the contacting can take place in vitro or in vivo with respect to the mammal. Preferably, the contacting is in vitro.

Also, detection of the complex can occur through any number of ways known in the art. For instance, the inventive antigen recognizing constructs (and functional variants thereof), polypeptides, proteins, nucleic acids, recombinant expression vectors, host cells, populations of cells, or antibodies or TCRs, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

For purposes of the inventive methods, wherein host cells or populations of cells are administered, the cells can be cells that are allogeneic or autologous to the mammal. Preferably, the cells are autologous to the mammal.

With respect to the above mentioned medical applications of the TCR material of the invention, the to be treated and/or diagnosed cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, chronic lymphocytic leukemia, chronic myeloid cancer, colon cancer, esophageal cancer, cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, and urinary bladder cancer. A preferred cancer is cancer is cancer of the uterine cervix, oropharynx, anus, anal canal, anorectum, vagina, vulva, or penis. A particularly preferred cancer is a TAA positive cancer, such as colon cancer, rectal cancer, gastrointestinal or gastric cancer.

In general, the invention provides a method for treating a subject suffering from a tumor or tumor disease comprising the administration of the antigen recognizing constructs, nucleic acids, vectors, pharmaceutical compositions and/or host cell as disclosed by the present invention. Preferably the subject is a subject in need of such a treatment. The subject in preferred embodiments is a mammalian subject, preferably a human patient, suffering from a tumor or tumor disease, which is TAA-positive.

In view of the disclosure herein it will be appreciated that the invention furthermore pertains to the following items:

Item 1: An antigen recognizing construct comprising at least one complementary determining region (CDR) 3 having at least 50% sequence identity to an amino acid sequence selected from SEQ ID NOs. 3, 9, 15, 21, 27 and 33.

Item 2: The antigen recognizing construct according to item 1, wherein said antigen recognizing construct is capable of specifically and/or selectively binding to a TAA of the invention antigenic peptide.

Item 3: The antigen recognizing construct according to item 1 or 2, wherein the antigen recognizing construct is an antibody, or derivative or fragment thereof, or a T cell receptor (TCR), or a derivative or fragment thereof.

Item 4: The antigen recognizing construct according to any one of items 1 to 3, wherein said antigen recognizing construct binds to a human leucocyte antigen (HLA) presented TAA antigenic peptide, wherein said HLA is optionally type A2.

Item 5: The antigen recognizing construct according to any one of items 1 to 4, wherein the construct specifically and/or selectively binds to an epitope comprising or consisting of the amino acid sequence selected from SEQ ID NOs: 49, and 50 to 57.

Item 6: The antigen recognizing construct according to any one of items 1 to 5, wherein the construct is an α/β-TCR, or fragment or derivative thereof, or the construct is a γ/δ-TCR, or a fragment or derivative thereof.

Item 7: The antigen recognizing construct according to any one of items 1 to 6, characterized in that the construct is of human origin and specifically and/or selectively recognizes a TAA antigenic peptide.

Item 8: The antigen recognizing construct according to any one of items 1 to 7, wherein said antigen recognizing construct is capable of inducing an immune response in a subject, optionally wherein the immune response is characterized by an increase in interferon (IFN) γ levels.

Item 9: The antigen recognizing construct according to any one of items 1 to 8, comprising a TCR α or γ chain; and/or a TCR β or δ chain; wherein the TCR α or γ chain comprises a CDR3 having at least 50%, 60%, 70%, 80%, 90%, 95%, 98%, 99%, or 100% sequence identity to an amino acid sequence selected from SEQ ID Nos. 3, 15, and 27, and/or wherein the TCR β or δ chain comprises a CDR3 having at least 50%, 60%, 70%, 80%, 90%, 95%, 98%, 99%, or 100% sequence identity to an amino acid sequence selected from SEQ ID Nos. 9, 21, and 33.

Item 10: The antigen recognizing construct according to item 9, wherein the TCR α or γ chain further comprises a CDR1 having at least 50%, 60%, 70%, 80%, 90%, 95%, 98%, 99%, or 100% sequence identity to an amino acid sequence selected from SEQ ID Nos. 1, 13, and 25; and/or a CDR2 having at least 50%, 60%, 70%, 80%, 90%, 95%, 98%, 99%, or 100% sequence identity to an amino acid sequence selected from SEQ ID Nos. 2, 14, and 26.

Item 11: The antigen recognizing construct according to item 9 or 10, wherein the TCR β or δ chain further comprises a CDR1 having at least 50%, 60%, 70%, 80%, 90%, 95%, 98%, 99%, or 100% sequence identity to an amino acid sequence selected from SEQ ID Nos. 7, 19, and 31; and/or a CDR2 having at least 50%, 60%, 70%, 80%, 90%, 95%, 98%, 99%, or 100% sequence identity to an amino acid sequence selected from SEQ ID Nos. 8, 20, and 32.

Item 12: The antigen recognizing construct according to any of items 1 to 11, comprising a TCR variable chain region having at least 50%, 60%, 70%, 80%, 90%, 95%, 98%, 99%, or 100% sequence identity to an amino acid sequence selected from SEQ ID Nos. 4, 10, 16, 22, 28, and 34.

Item 13: The antigen recognizing construct according to any of items 1 to 12, wherein the construct is humanized, chimerized and/or murinized.

Item 14: The antigen recognizing construct according to any of items 1 to 13, comprising a binding fragment of a TCR, and wherein said binding fragment comprises CDR1 to CDR3 optionally selected from the CDR1 to CDR3 sequences having the amino acid sequences of SEQ ID Nos. 1, 2, 3, or 7, 8, 9 or 13, 14, 15, or 19, 20, 21, or 25, 26, 27 or 31, 32, 33.

Item 15: The antigen recognizing construct according to any of items 1 to 14, wherein the construct is a TCR, or a fragment thereof, composed of at least one TCR α and one TCR β chain sequence, wherein said TCR α chain sequence comprises the CDR1 to CDR3 sequences having the amino acid sequences of SEQ ID NO: 1 to 3, and said TCR β chain sequence comprises the CDR1 to CDR3 sequences having the amino acid sequences of SEQ ID NO: 7 to 9; or wherein said TCR α chain sequence comprises the CDR1 to CDR3 sequences having the amino acid sequences of SEQ ID NO: 13 to 15, and said TCR β chain sequence comprises the CDR1 to CDR3 sequences having the amino acid sequences of SEQ ID NO: 19 to 21; or wherein said TCR α chain sequence comprises the CDR1 to CDR3 sequences having the amino acid sequences of SEQ ID NO: 25 to 27, and said TCR β chain sequence comprises the CDR1 to CDR3 sequences having the amino acid sequences of SEQ ID NO: 31 to 33.

Item 16: The antigen recognizing construct according to any of items 1 to 15, wherein the construct is a TCR, or a fragment thereof, comprising at least one TCR α and one TCR β chain sequence, wherein said TCR α chain sequence comprises a variable region sequence having the amino acid sequence of SEQ ID No. 4, and wherein said TCR β chain sequence comprises a variable region sequence having the amino acid sequence of SEQ ID No. 10; or wherein said TCR α chain sequence comprises a variable region sequence having the amino acid sequence of SEQ ID No. 16, and wherein said TCR β chain sequence comprises a variable region sequence having the amino acid sequence of SEQ ID No. 22; or wherein said TCR α chain sequence comprises a variable region sequence having the amino acid sequence of SEQ ID No. 28, and wherein said TCR β chain sequence comprises a variable region sequence having the amino acid sequence of SEQ ID No. 34.

Item 17: The antigen recognizing construct according to any of items 1 to 16, wherein the construct is a TCR, or a fragment thereof, further comprising a TCR constant region having at least 50%, 60%, 70%, 80%, 90%, 95%, 98%, 99%, or 100% sequence identity to an amino acid sequence selected from SEQ ID Nos. 5, 11, 17, 23, 29 and 35, preferably wherein the TCR is composed of at least one TCR α and one TCR β chain sequence, wherein the TCR α chain sequence comprises a constant region having at least 50%, 60%, 70%, 80%, 90%, 95%, 98%, 99%, or 100% sequence identity to an amino acid sequence selected from SEQ ID Nos. 5, 17, and 29.

Item 18: The antigen recognizing construct according to any of items 1 to 17, comprising a first TCR chain having at least 50%, 60%, 70%, 80%, 90%, 95%, 98%, 99%, or 100% sequence identity to the amino acid sequence of SEQ ID No. 6, and a second TCR chain having at least 50%, 60%, 70%, 80%, 90%, 95%, 98%, 99%, or 100% sequence identity to the amino acid sequence of SEQ ID No. 12.

Item 19: The antigen recognizing construct according to any of items 1 to 17, comprising a first TCR chain having at least 50%, 60%, 70%, 80%, 90%, 95%, 98%, 99%, or 100% sequence identity to the amino acid sequence of SEQ ID No. 18, and a second TCR chain having at least 50%, 60%, 70%, 80%, 90%, 95%, 98%, 99%, or 100% sequence identity to the amino acid sequence of SEQ ID No. 24.

Item 20: The antigen recognizing construct according to any of items 1 to 17, comprising a first TCR chain having at least 50%, 60%, 70%, 80%, 90%, 95%, 98%, 99%, or 100% sequence identity to the amino acid sequence of SEQ ID No. 30, and a second TCR chain having at least 50%, 60%, 70%, 80%, 90%, 95%, 98%, 99%, or 100% sequence identity to the amino acid sequence of SEQ ID No. 36.

Item 21: A nucleic acid encoding for an antigen recognizing construct according to any one of items 1 to 20.

Item 22: A vector comprising a nucleic acid according to item 21.

Item 23: A host cell comprising an antigen recognizing construct according to any one of items 1 to 20, or a nucleic acid according to item 21, or a vector according to item 22.

Item 24: The host cell according to item 23, wherein the cell is a lymphocyte, preferably a T lymphocyte or T lymphocyte progenitor, more preferably a CD4 or CD8 positive T-cell.

Item 25: A pharmaceutical composition comprising the antigen recognizing construct according to any of items 1 to 20, or the nucleic acid according to item 21, or the vector according to item 22, or the host cell according to item 23 or 24, and a pharmaceutical acceptable carrier, stabilizer and/or excipient.

Item 26: The antigen recognizing construct according to any one of items 1 to 20, or a nucleic acid according to item 21, or a vector according to item 22, or a host cell according to item 23 or 24, or the pharmaceutical composition according to item 25, for use in medicine.

Item 27: The antigen recognizing construct, or the nucleic acid, or the vector, or the host cell, or the pharmaceutical composition, for use according to item 26, for use in the diagnosis, prevention, and/or treatment of a proliferative disease, wherein the disease comprises a malignant or benign tumor disease.

Item 28: The antigen recognizing construct, or the nucleic acid, or the vector, or the host cell, or the pharmaceutical composition, for use according to item 27, wherein the tumor disease is characterized by the expression of TAA in a tumor cell of the tumor disease.

Item 29: The antigen recognizing construct, or the nucleic acid, or the vector, or the host cell, or the pharmaceutical composition, for use according to any one of items 26 to 28, wherein the use in medicine is a use in immune therapy optionally comprising an adoptive cell transfer, wherein the immune therapy comprises adoptive autologous or heterologous T-cell therapy.

Item 30: A method of manufacturing a TAA specific antigen recognizing construct expressing cell line, comprising
a. providing a suitable host cell,
b. providing a genetic construct comprising a coding sequence encoding the antigen recognizing construct according to any of items 1 to 20,
c. introducing into said suitable host cell said genetic construct,
d. expressing said genetic construct by said suitable host cell.

Item 31: The method according to item 30, further comprising cell surface presentation of said antigen recognizing construct.

Item 32: The method according to item 30 or 31, wherein the genetic construct is an expression construct comprising a promoter sequence operably linked to said coding sequence.

Item 33: The method according to any one of items 30 to 32, wherein said antigen recognizing construct is of mammalian origin, preferably of human origin.

Item 34: The method according to any one of items 30 to 33, wherein said suitable host cell is a mammalian cell, optionally selected from a human cell or a human T lymphocyte.

Item 35: The method according to any of items 30 to 34, wherein said antigen recognizing construct is a modified TCR, wherein said modification comprises addition of a functional domain comprising a label, or an alternative domain comprising a membrane anchor domain.

Item 36: The method according to item 35, wherein said antigen recognizing construct is an alpha/beta TCR, gamma/delta TCR, or a single chain TCR (scTCR).

Item 37: The method according to any of items 30 to 36, wherein said genetic construct is introduced into said suitable host cell by retroviral transfection.

Item 38: The method according to any of items 30 to 37, further comprising the isolation and purification of the antigen recognizing construct from the suitable host cell and, optionally, reconstitution of the antigen recognizing construct in a T-cell.

Item 39: A method of treating cancer comprising administering to a subject in need thereof the TCR, the nucleic acid or the expression vector, the host cell, and/or the pharmaceutical composition of any of the above items.

Item 40: The method of item 39, wherein the TCR is expressed on the surface of a host cell.

Item 41: The method of item 40, wherein the host cell is selected from the group consisting of a T cell or T cell progenitor.

Item 42: The method of item 41, wherein the T cell or T cell progenitor is autologous.

Item 43: The method of item 42, wherein the T cell or T cell progenitor is allogeneic.

Item 44: The method of item 43, wherein the TCR is conjugated to a therapeutically active agent.

Item 45: The method of item 44, wherein the therapeutically active agent is selected from the group consisting of a radionuclide, a chemotherapeutic agent and a toxin.

Item 46: The method of any of items 39 to 45, wherein the cancer is non-small cell lung cancer, small cell lung cancer, renal cell cancer, brain cancer, gastric cancer, colorectal cancer, hepatocellular cancer, head and neck cancer, pancreatic cancer, prostate cancer, leukemia, breast cancer, Merkel cell carcinoma, melanoma, ovarian cancer, urinary bladder cancer, uterine cancer, gallbladder and bile duct cancer, esophageal cancer, or a combination thereof.

Item 47: The method of any of items 39 to 46, further comprising administering to the subject at least one chemotherapeutic agent.

Item 48: The method of any of items 46 to 47, further comprising administering radiation therapy to the subject.

Item 49: A method of treating cancer in a subject in need thereof, comprising:
a) isolating a cell from said subject;
b) transforming the cell with a vector encoding the TCR of any of the items above to produce a transformed cell;
c) expanding the transformed cell to produce a plurality of transformed cells; and
d) administering the plurality of transformed cells to said subject.

Item 50: The method of Item 49, wherein the cell is selected from a T cell or a T cell progenitor.

Item 51: A method of treating cancer in a subject in need thereof, comprising:
a) isolating a cell from a healthy donor;
b) transforming the cell with a vector encoding the TCR of any of the items above to produce a transformed cell;
c) expanding the transformed cell to produce a plurality of transformed cells; and
d) administering the plurality of transformed cells to said subject.

Item 52: The method of Item 51, wherein the cell is selected from a T cell or a T cell progenitor.

The present invention will now be further described in the following examples with reference to the accompanying figures and sequences, nevertheless, without being limited thereto. For the purposes of the present invention, all references as cited herein are incorporated by reference in their entireties. In the Figures and Sequences:

FIG. 1: IFNγ release from CD8+ T-cells electroporated with alpha and beta chain RNA of TCR R36P3F9 (Table 1) after co-incubation with T2 target cells loaded with the DCAF4L2-001 peptide (SEQ ID NO:49) or various DCAF4L2-001 alanine-substitution variants at positions 1-9 of SEQ ID NO:1 (SEQ ID NOs: 50-58) or control peptide NYESO1-001 (SEQ ID NO: 69). IFNγ release data were obtained with CD8+ T-cells derived from two different healthy donors. RNA electroporated CD8+ T-cells alone or in co-incubation with unloaded target cells served as controls.

Figure 2:
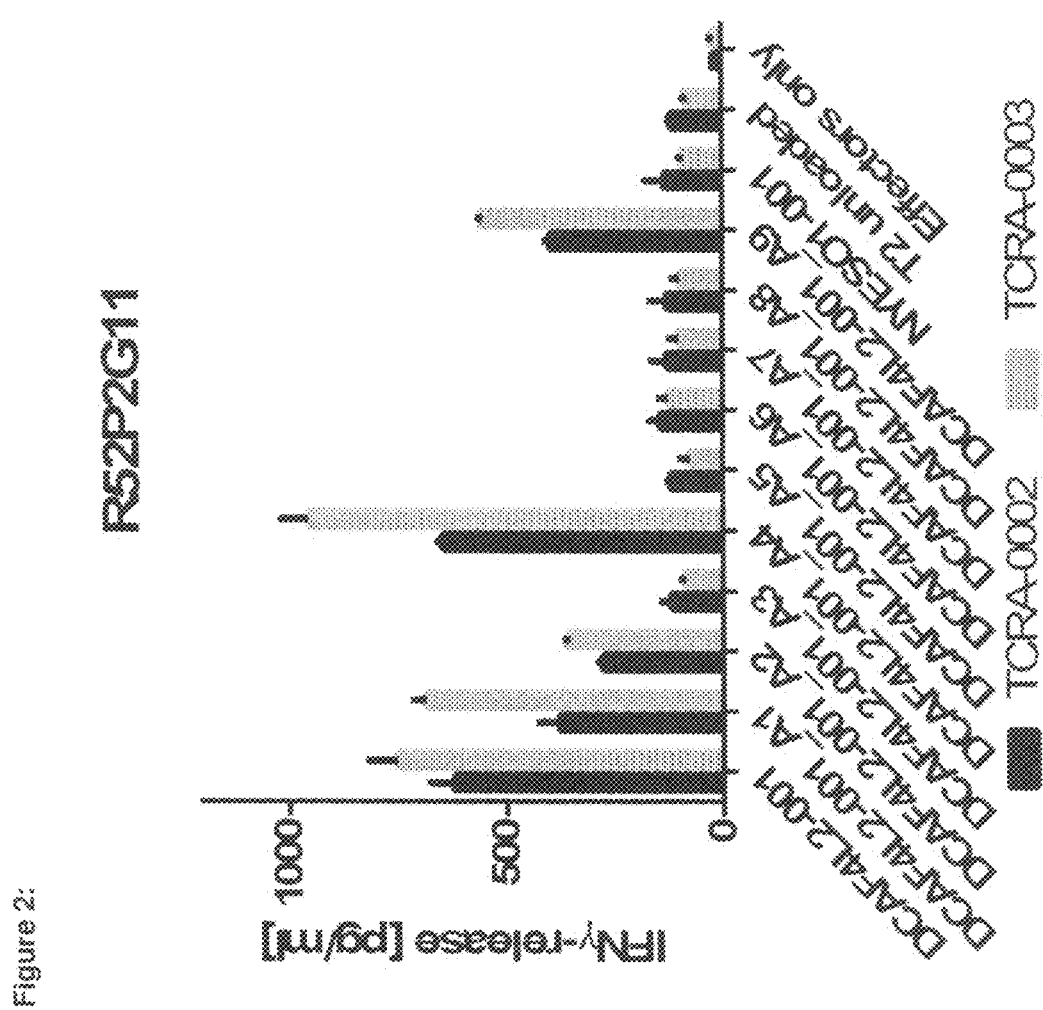

FIG. 2: IFNγ release from CD8+ T-cells electroporated with alpha and beta chain RNA of TCR R52P2G11 (Table 1) after co-incubation with T2 target cells loaded with DCAF4L2-001 peptide (SEQ ID NO: 49) or various DCAF4L2-001 alanine-substitution variants at positions 1-9 of SEQ ID NO:1 (SEQ ID NOs: 50 to 58) or control peptide NYESO1-001 (SEQ ID NO: 69). IFNγ release data were obtained with CD8+ T-cells derived from two different healthy donors. RNA electroporated CD8+ T-cells alone or in co-incubation with unloaded target cells served as controls.

Figure 3:
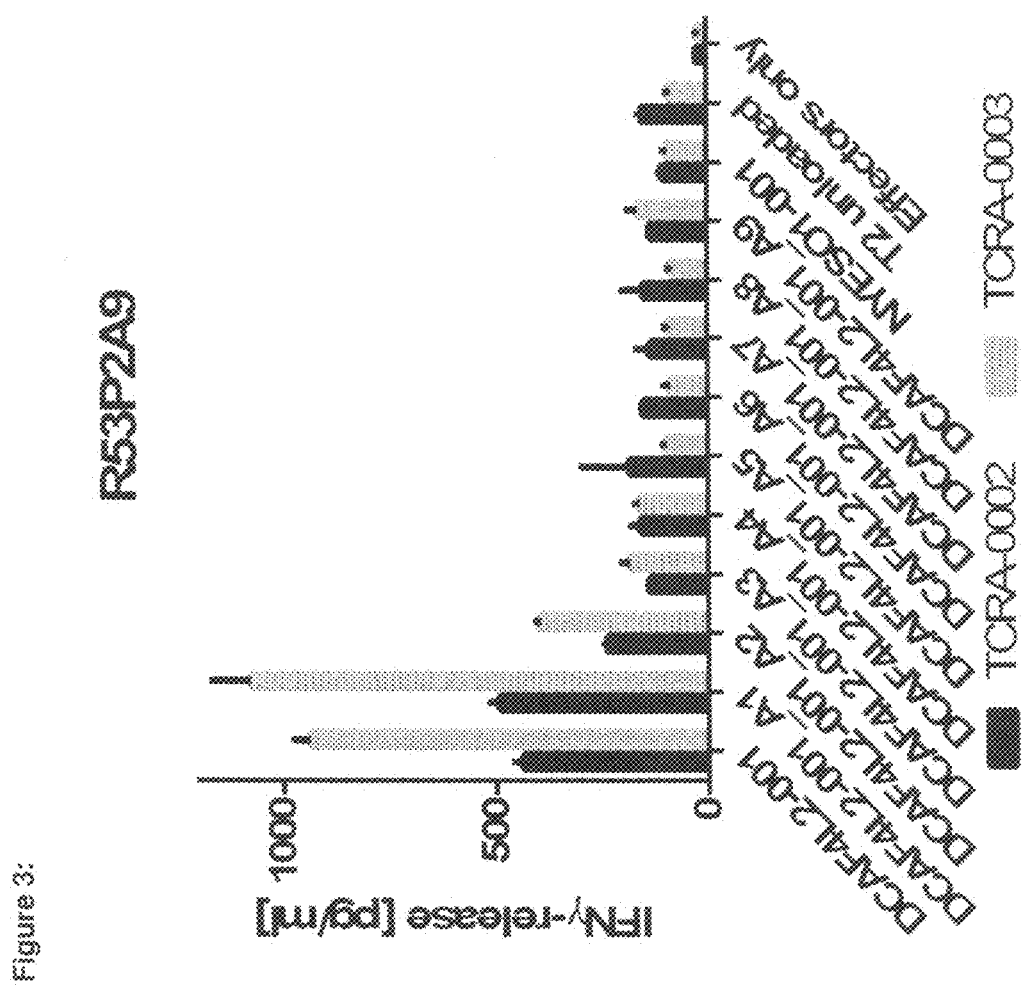

FIG. 3: IFNγ release from CD8+ T-cells electroporated with alpha and beta chain RNA of TCR R53P2A9 (Table 1) after co-incubation with T2 target cells loaded with DCAF4L2-001 peptide (SEQ ID NO: 49) or various DCAF4L2-001 alanine-substitution variants at positions 1-9 of SEQ ID NO:1 (SEQ ID NOs: 50 to 58) or control peptide NYESO1-001 (SEQ ID NO: 69). IFNγ release data were obtained with CD8+ T-cells derived from two different healthy donors. RNA electroporated CD8+ T-cells alone or in co-incubation with unloaded target cells served as controls.

Figure 4:
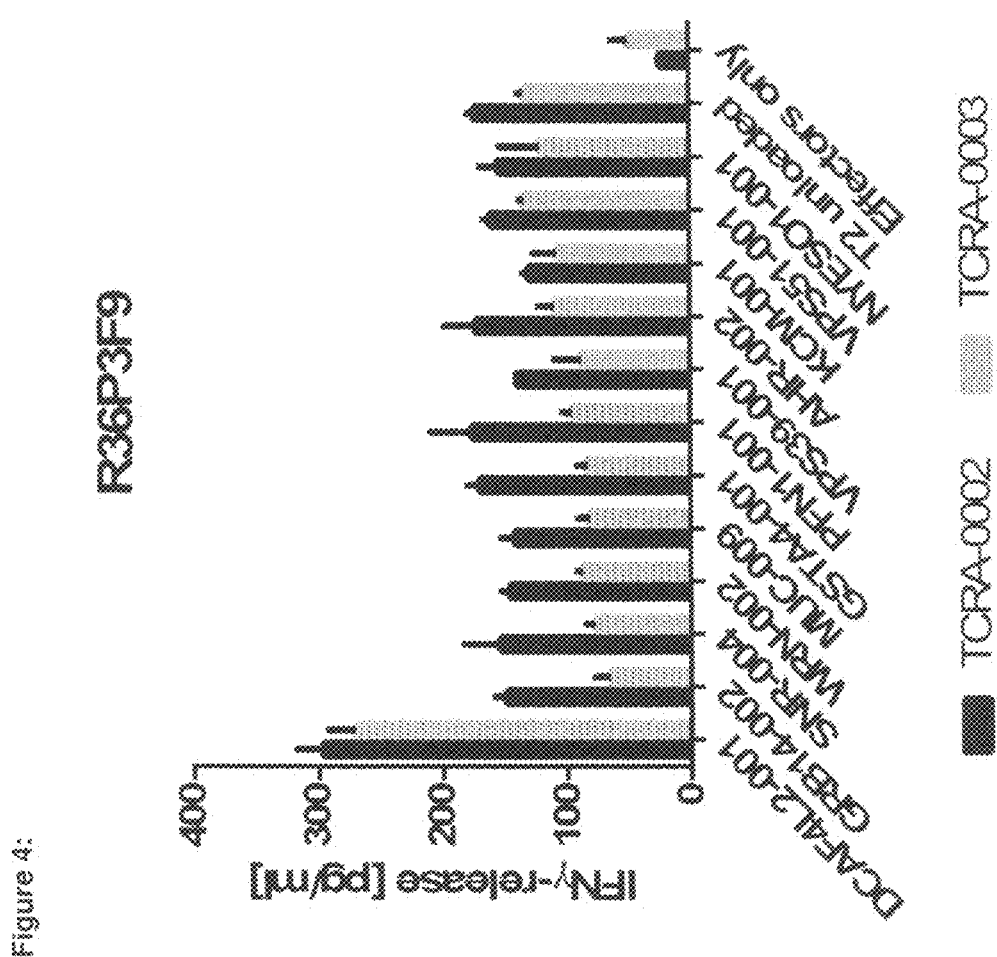

FIG. 4: IFNγ release from CD8+ T-cells electroporated with alpha and beta chain RNA of TCRs R36P3F9 after co-incubation with T2 target cells loaded with DCAF4L2-001 peptide (SEQ ID NO:49) or homologous but unrelated peptide GRB14-002 (SEQ ID NO:59), SNR-004 (SEQ ID NO:60), WRN-002 (SEQ ID NO:61), MUC-009 (SEQ ID NO:62), GSTA4-001 (SEQ ID NO:63), PFN1-001 (SEQ ID NO:64), VPS39-001 (SEQ ID NO:65), AHR-002 (SEQ ID NO:66), KCM-001 (SEQ ID NO:67) or VPS51-001 (SEQ ID NO:68) or control peptide NYESO1-001 (SEQ ID NO:69). IFNγ release data were obtained with CD8+ T-cells derived from two different healthy donors. RNA electroporated CD8+ T-cells alone or in co-incubation with unloaded target cells served as controls.

Figure 5:
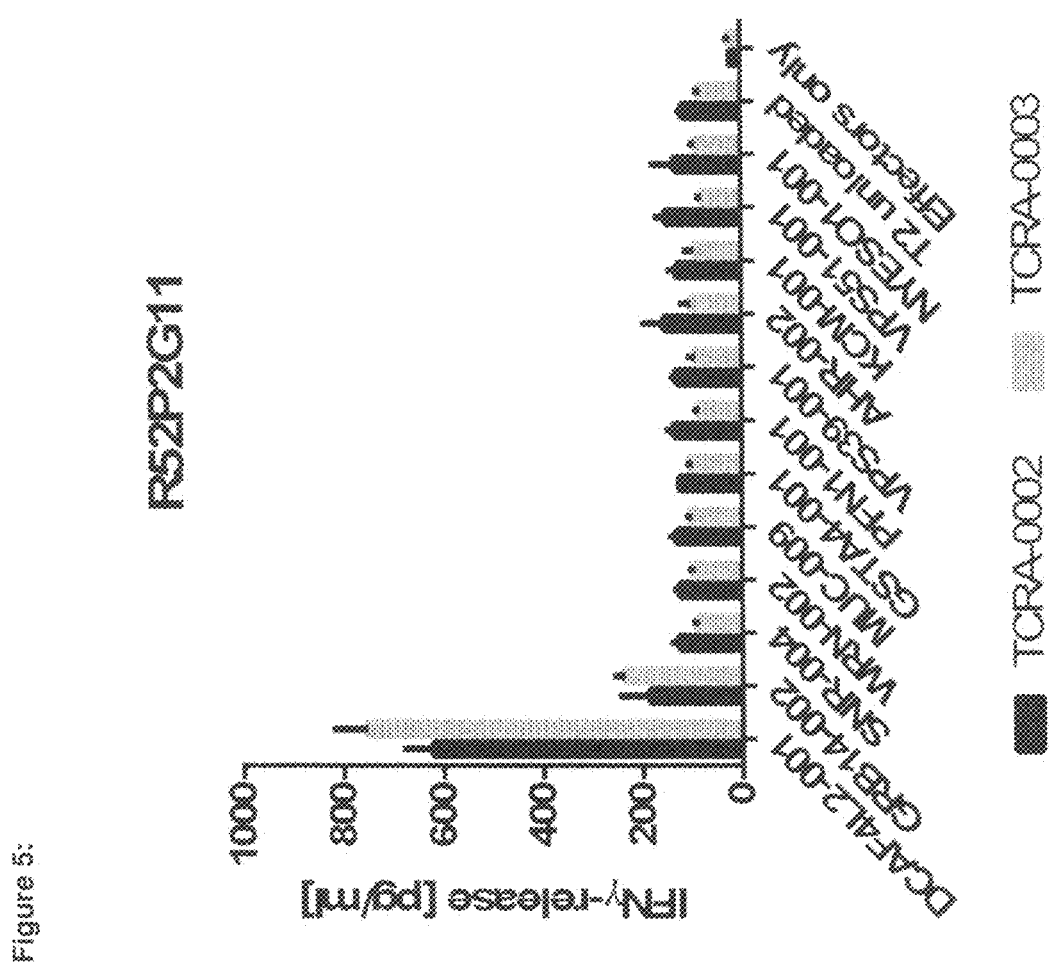

FIG. 5: IFNγ release from CD8+ T-cells electroporated with alpha and beta chain RNA of TCRs R52P2G11 after co-incubation with T2 target cells loaded with DCAF4L2-001 peptide (SEQ ID NO:49) or homologous but unrelated peptide GRB14-002 (SEQ ID NO:59), SNR-004 (SEQ ID NO:60), WRN-002 (SEQ ID NO:61), MUC-009 (SEQ ID NO:62), GSTA4-001 (SEQ ID NO:63), PFN1-001 (SEQ ID NO:64), VPS39-001 (SEQ ID NO:65), AHR-002 (SEQ ID NO:66), KCM-001 (SEQ ID NO:67) or VPS51-001 (SEQ ID NO:68) or control peptide NYESO1-001 (SEQ ID NO:69). IFNγ release data were obtained with CD8+ T-cells derived from two different healthy donors. RNA electroporated CD8+ T-cells alone or in co-incubation with unloaded target cells served as controls.

Figure 6:
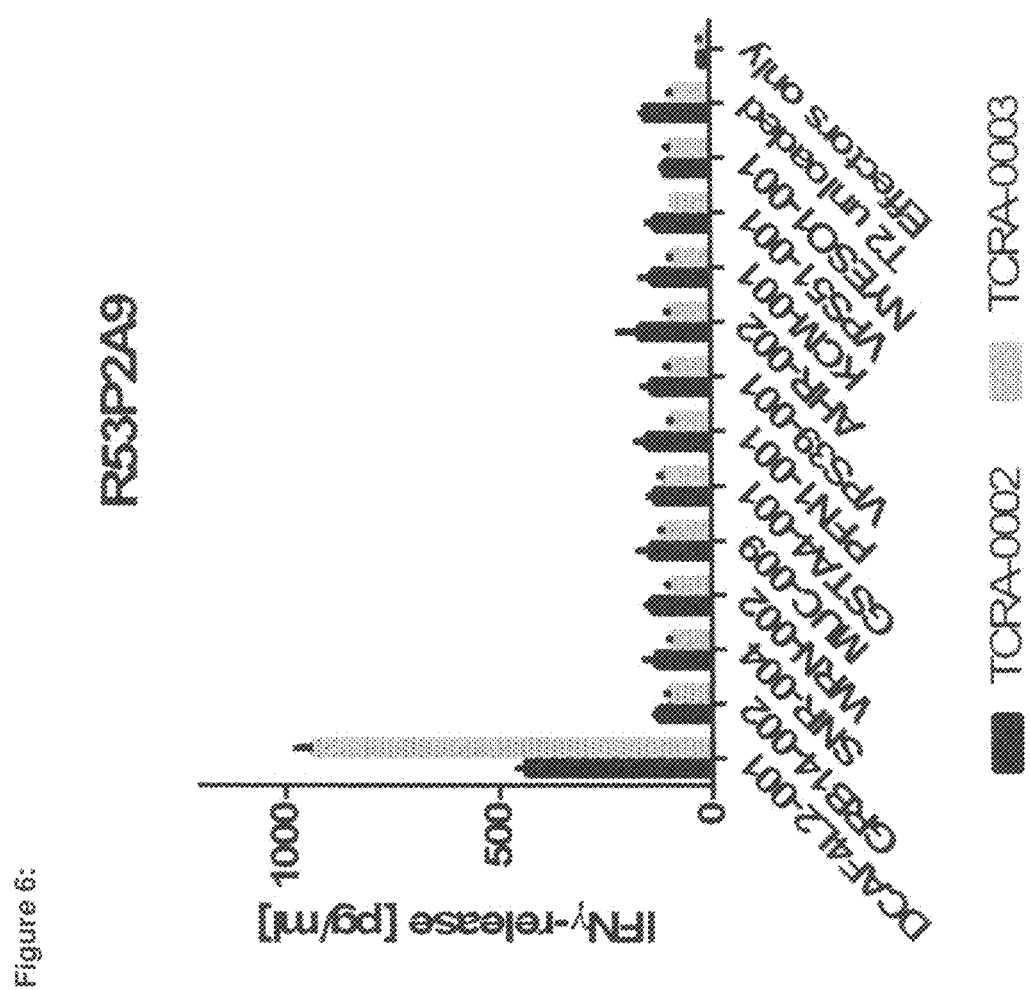

FIG. 6: IFNγ release from CD8+ T-cells electroporated with alpha and beta chain RNA of TCRs R53P2A9 after co-incubation with T2 target cells loaded with DCAF4L2-001 peptide (SEQ ID NO:49) or homologous but unrelated peptide GRB14-002 (SEQ ID NO:59), SNR-004 (SEQ ID NO:60), WRN-002 (SEQ ID NO:61), MUC-009 (SEQ ID NO:62), GSTA4-001 (SEQ ID NO:63), PFN1-001 (SEQ ID NO:64), VPS39-001 (SEQ ID NO:65), AHR-002 (SEQ ID NO:66), KCM-001 (SEQ ID NO:67) or VPS51-001 (SEQ ID NO:68) or control peptide NYESO1-001 (SEQ ID NO:69). IFNγ release data were obtained with CD8+ T-cells derived from two different healthy donors. RNA electroporated CD8+ T-cells alone or in co-incubation with unloaded target cells served as controls.

Figure 7:
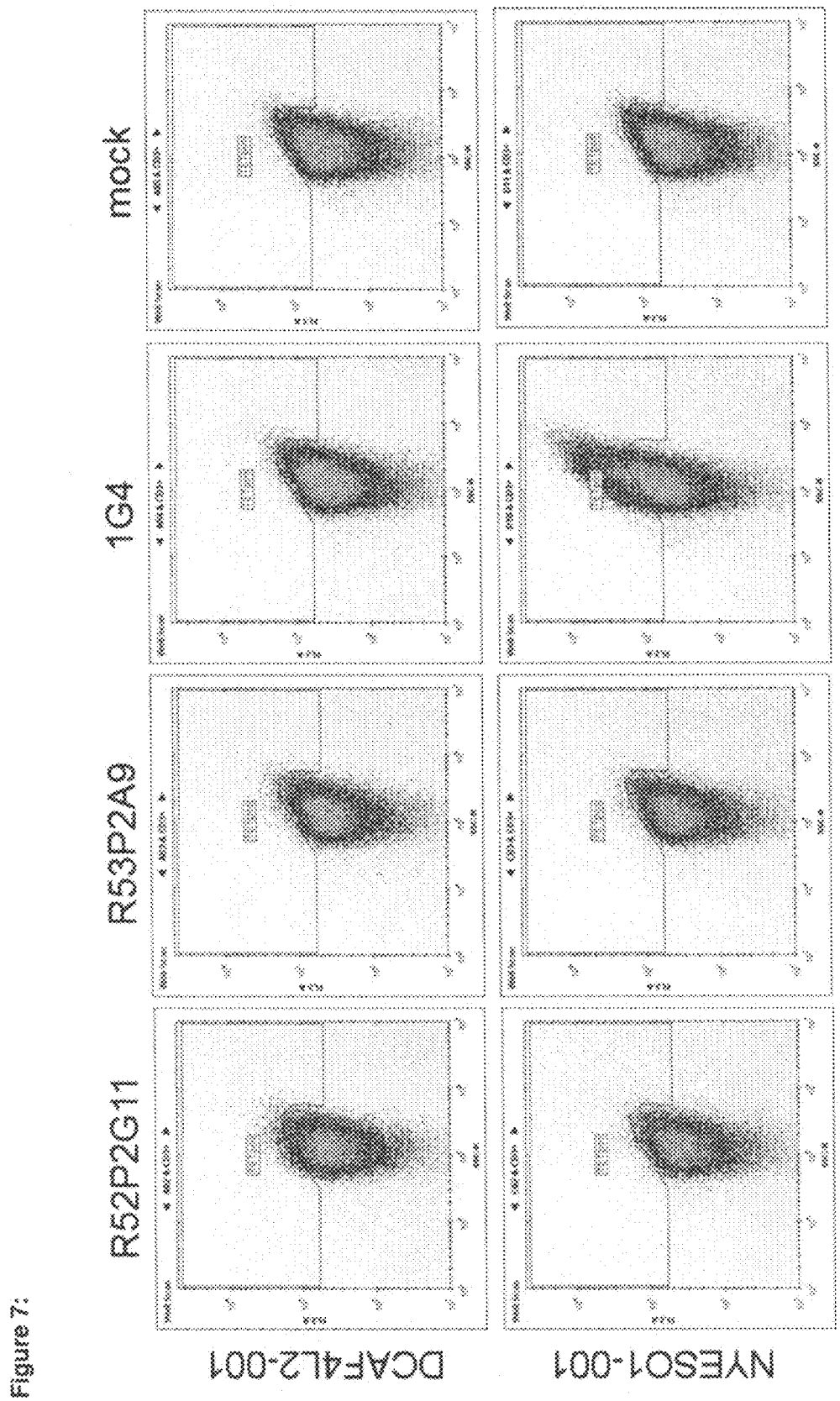

FIG. 7: HLA-A*02/DCAF4L2-001 tetramer or HLA-A*02/NYESO1-001 tetramer staining, respectively, of CD8+ T-cells electroporated with alpha and beta chain RNA of TCRs R52P2G11 and R53P2A9, respectively. CD8+ T-cells electroporated with RNA of 1G4 TCR that specifically binds to HLA-A*02/NYESO1-001 complex and mock electroporated CD8+ T-cells served as controls.

Figure 8:
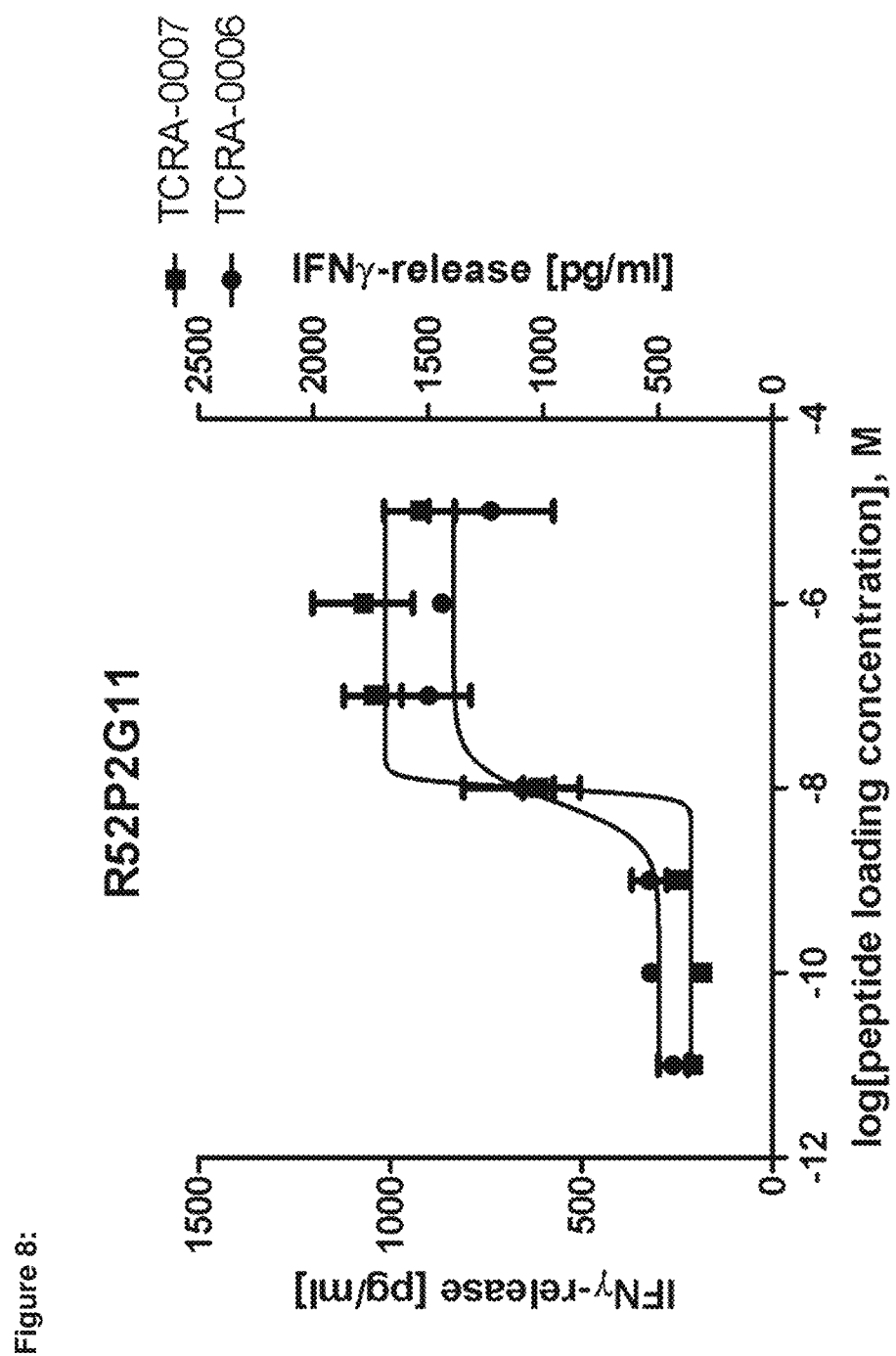

FIG. 8: IFNγ release from CD8+ T-cells electroporated with alpha and beta chain RNA of TCR R52P2G11 (Table 1) after co-incubation with T2 target cells loaded with DCAF4L2-001 peptide (SEQ ID NO:49) in various peptide loading concentrations from 10 μM to 10 pM. IFNγ release data were obtained with CD8+ T-cells derived from two different healthy donors. RNA electroporated CD8+ T-cells alone or in co-incubation with unloaded target cells served as controls. Donor 1 (TCRA-0006) is shown on the left Y-axis, donor 2 (TCRA-0007) on the right Y-axis, respectively.

Figure 9:
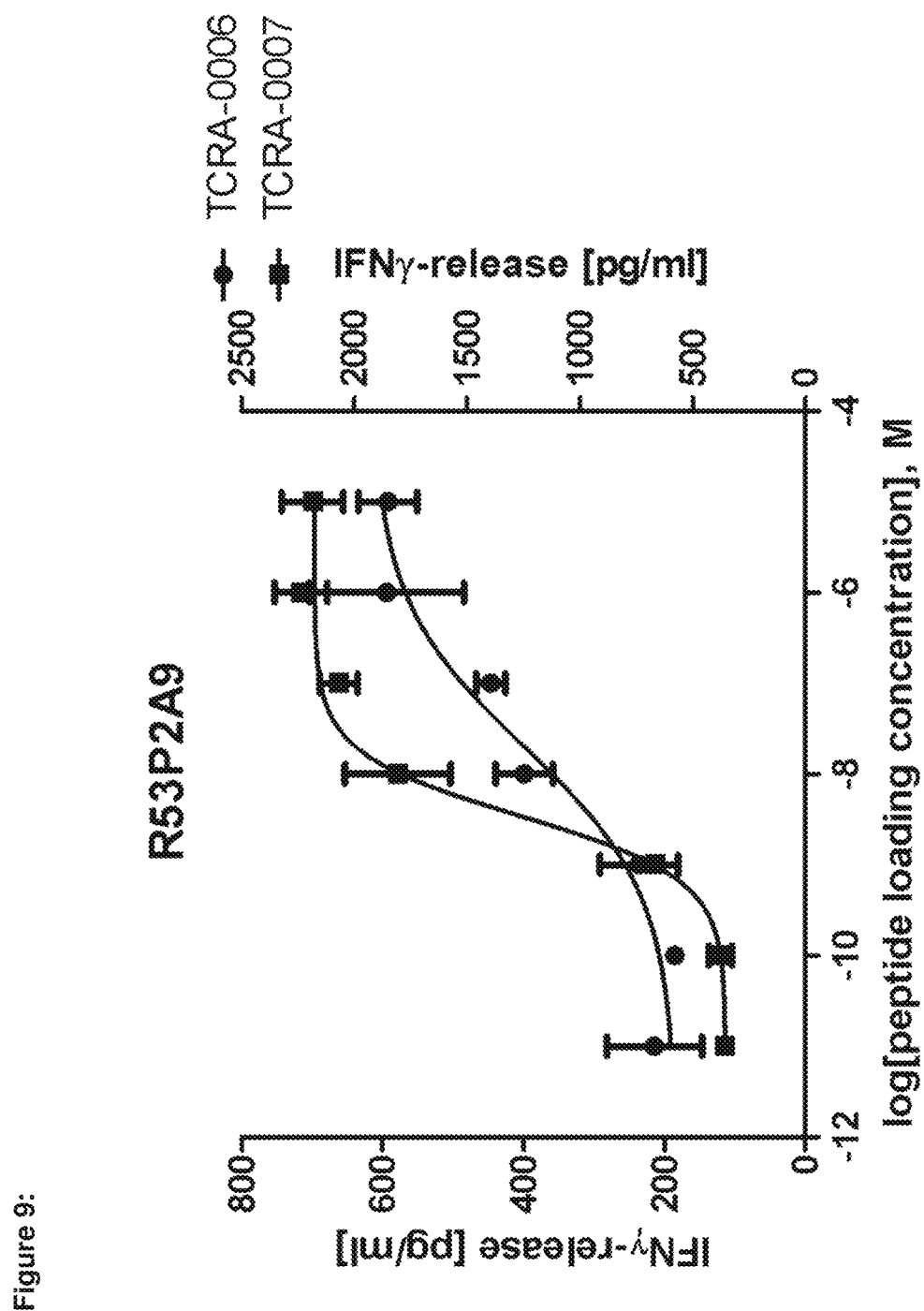

FIG. 9: IFNγ release from CD8+ T-cells electroporated with alpha and beta chain RNA of TCR R53P2A9 (Table 1) after co-incubation with T2 target cells loaded with DCAF4L2-001 peptide (SEQ ID NO:49) in various peptide loading concentrations from 10 μM to 10 pM. IFNγ release data were obtained with CD8+ T-cells derived from two different healthy donors. RNA electroporated CD8+ T-cells alone or in co-incubation with unloaded target cells served as controls. Donor 1 (TCRA-0006) is shown on the left Y-axis, donor 2 (TCRA-0007) on the right Y-axis, respectively.

Figure 10:
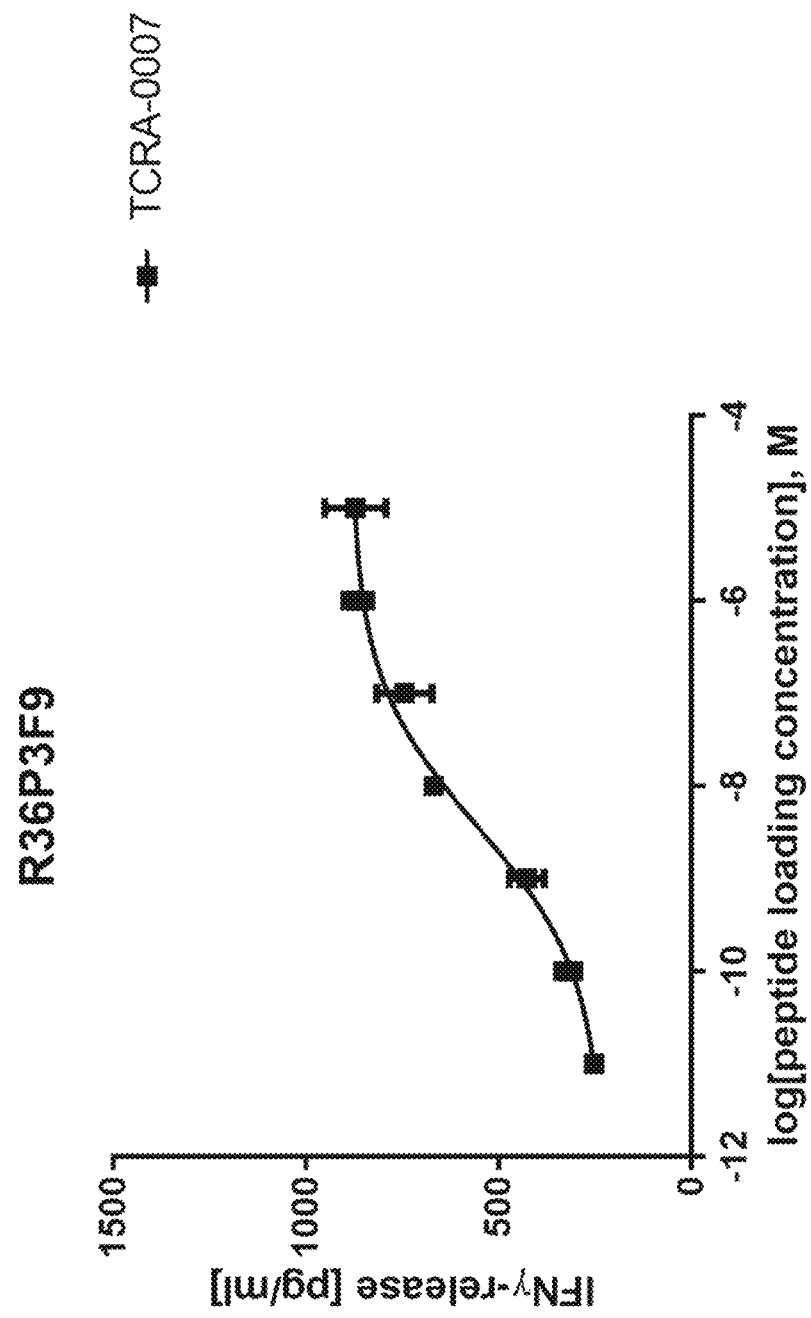

FIG. 10: IFNγ release from CD8+ T-cells electroporated with alpha and beta chain RNA of TCR R36P3F9 (Table 1) after co-incubation with T2 target cells loaded with DCAF4L2-001 peptide (SEQ ID NO:49) in various peptide loading concentrations from 10 μM to 10 pM. RNA electroporated CD8+ T-cells alone or in co-incubation with unloaded target cells served as controls.

Figure 11:
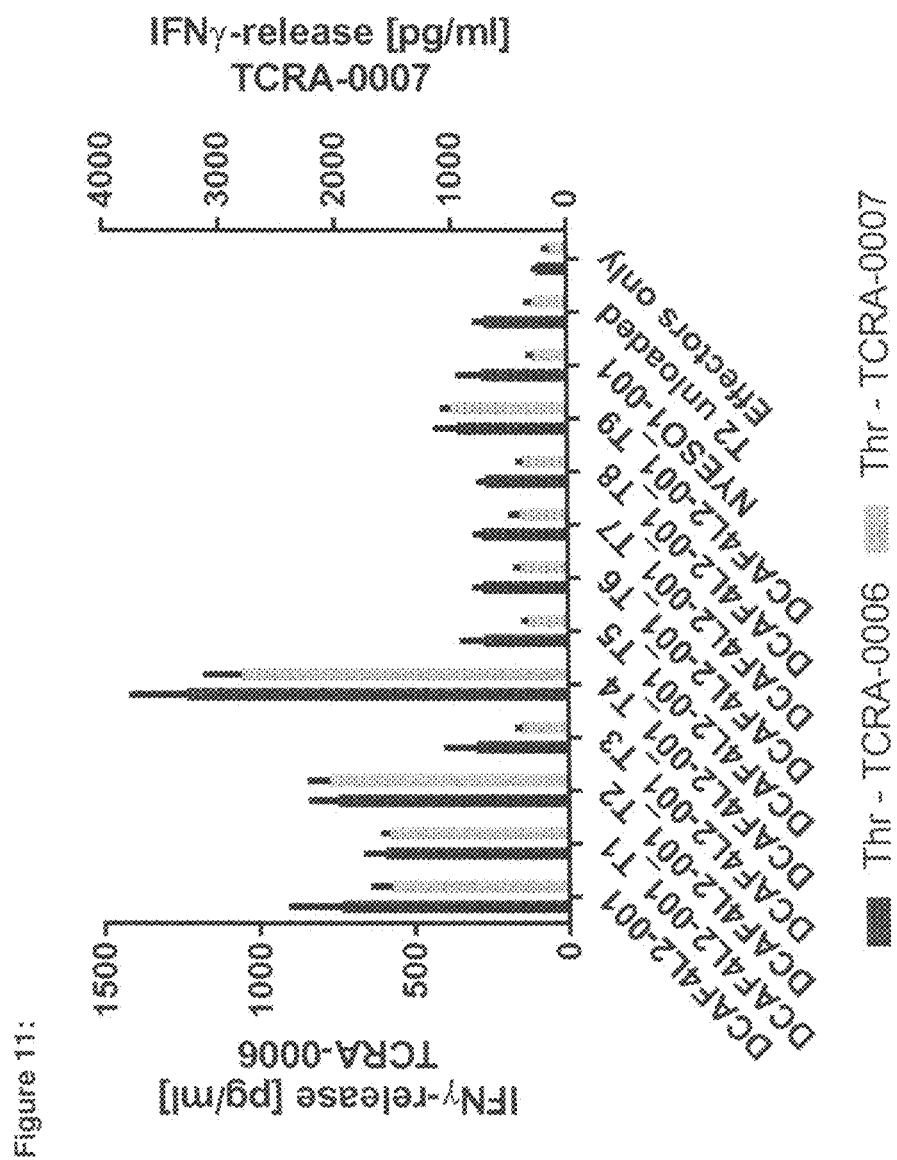

FIG. 11: IFNγ release from CD8+ T-cells electroporated with alpha and beta chain RNA of TCR R52P2G11 (Table 1) after co-incubation with T2 target cells loaded with DCAF4L2-001 peptide (SEQ ID NO: 49) or various DCAF4L2-001 threonine-substitution variants at positions 1-9 of SEQ ID NO:1 (SEQ ID NOs: 70 to 78) or control peptide NYESO1-001 (SEQ ID NO: 69). IFNγ release data were obtained with CD8+ T-cells derived from two different healthy donors. RNA electroporated CD8+ T-cells alone or in co-incubation with unloaded target cells served as controls.

Figure 12:
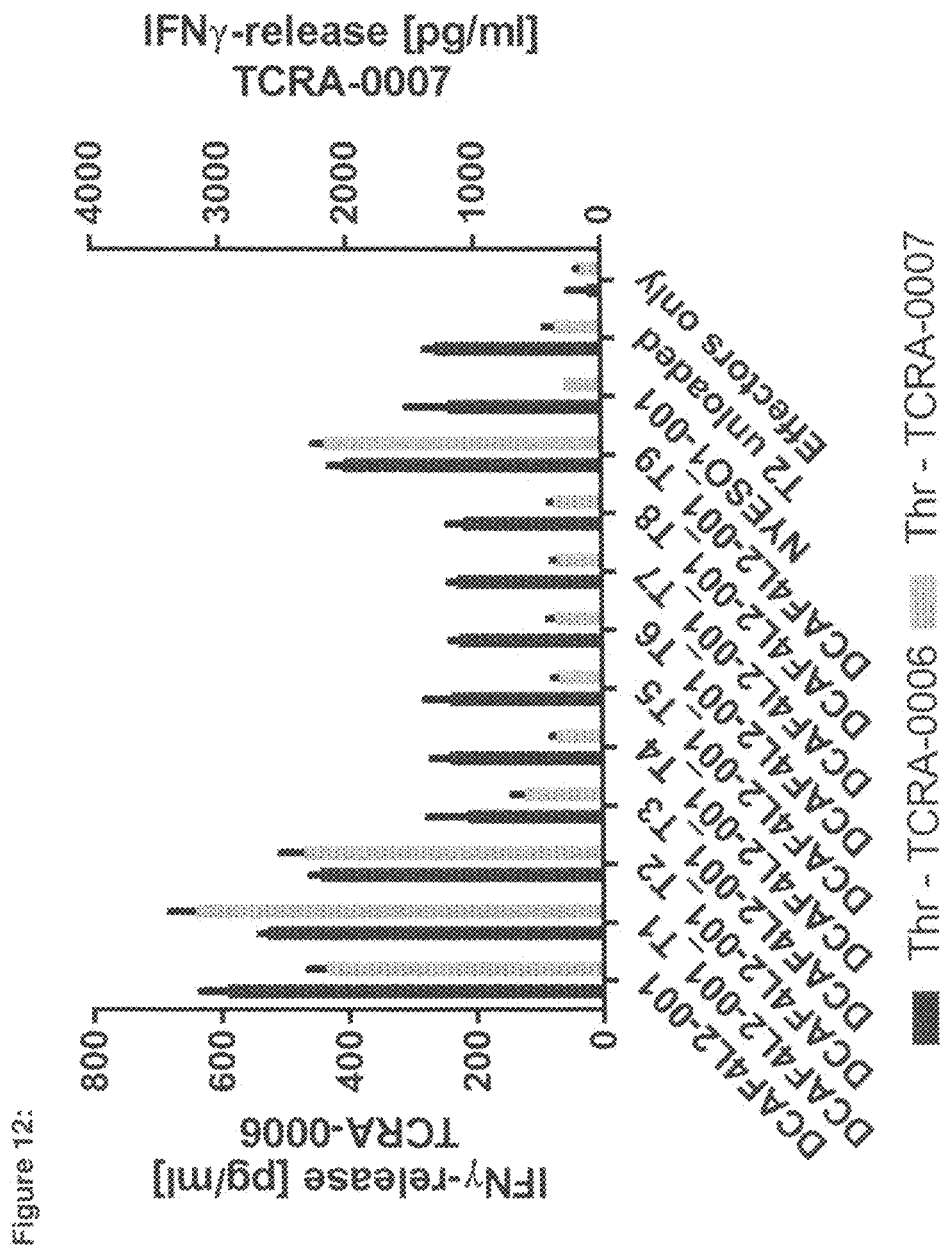

FIG. 12: IFNγ release from CD8+ T-cells electroporated with alpha and beta chain RNA of TCR R53P2A9 (Table 1) after co-incubation with T2 target cells loaded with DCAF4L2-001 peptide (SEQ ID NO: 49) or various DCAF4L2-001 threonine-substitution variants at positions 1-9 of SEQ ID NO:1 (SEQ ID NOs: 70 to 78) or control peptide NYESO1-001 (SEQ ID NO: 69). IFNγ release data were obtained with CD8+ T-cells derived from two different healthy donors. RNA electroporated CD8+ T-cells alone or in co-incubation with unloaded target cells served as controls.

Figure 13:
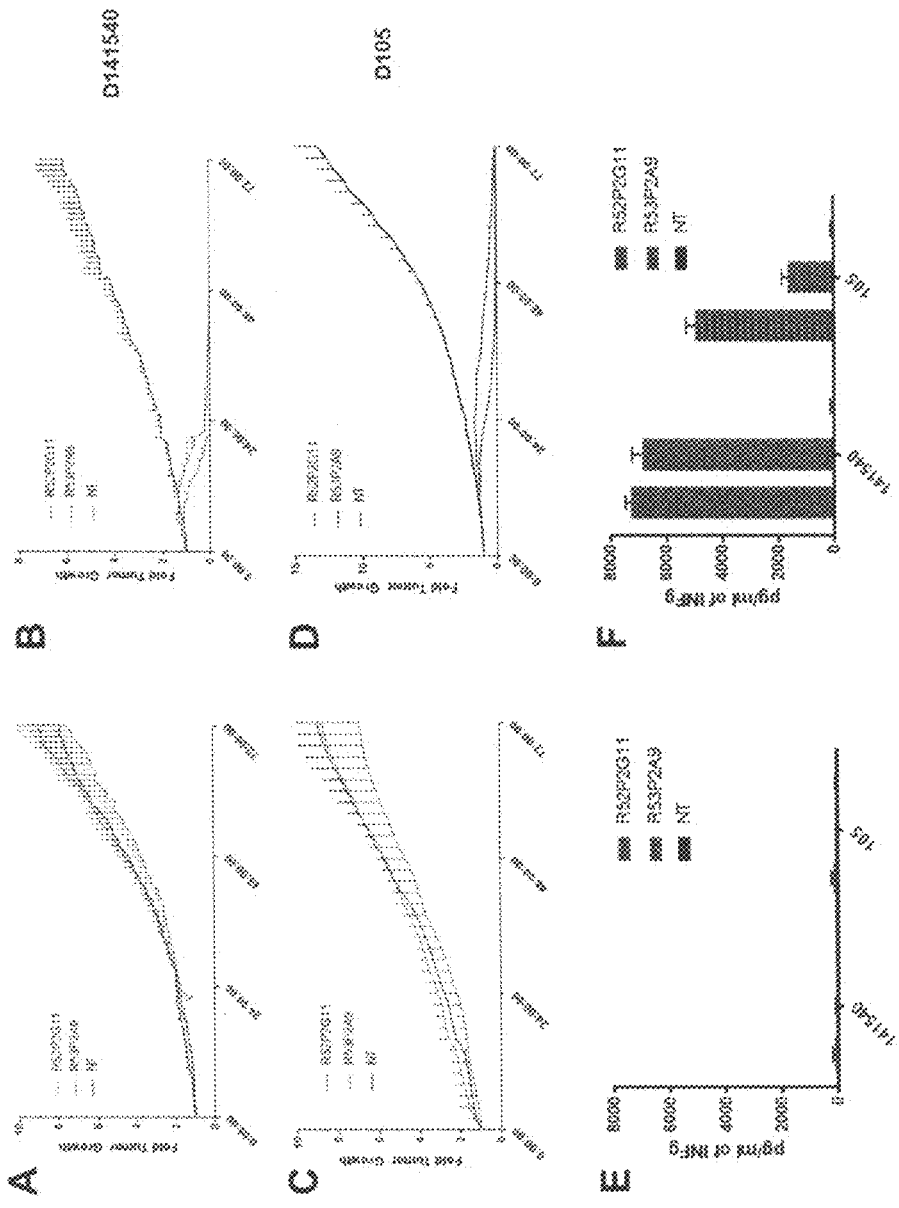

FIG. 13: Effect on tumor growth (A, B, C, D) and IFNγ release (E, F) of T-cells after lentiviral transduction with different constructs containing alpha and beta chain of TCR R52P2G11 or R53P2A9 to assess TCR-mediated recognition of endogenously processed and presented DCAF4L2-001 in DCAF4L2-expressing A375 cells (B, D, F). Target-negative A375 cells served as control (A, C, E). Data shown from 2 Donors; 141540 (A, B, E, F) and 105 (C, D, E, F).

TABLE 1

TCR sequences of the invention

| SEQ ID NO: | TCR name | Chain | Region | Sequence |
|---|---|---|---|---|
| 1 | R36P3F9 | alpha | CDR1 | TSINN |
| 2 | R36P3F9 | alpha | CDR2 | IRS |
| 3 | R36P3F9 | alpha | CDR3 | CATVSNYQLIW |
| 4 | R36P3F9 | alpha | variable domain | METLLGVSLVILWLQLARVNSQQGEED PQALSIQEGENATMNCSYKTSINNLQW |

TABLE 1-continued

TCR sequences of the invention

| SEQ ID NO: | TCR name | Chain | Region | Sequence |
|---|---|---|---|---|
| | | | | YRQNSGRGLVHLILIRSNEREKHSGRLR VTLDTSKKSSSLLITASRAADTASYFCAT VSNYQLIWGAGTKLIIKP |
| 5 | R36P3F9 | alpha | constant domain | DIQNPDPAVYQLRDSKSSDKSVCLFTDF DSQTNVSQSKDSDVYITDKTVLDMRSM DFKSNSAVAWSNKSDFACANAFNNSIIP EDTFFPSPESSCDVKLVEKSFETDTNLN FQNLSVIGFRILLLKVAGFNLLMTLRLWS S |
| 6 | R36P3F9 | alpha | full-length | METLLGVSLVILWLQLARVNSQQGEED PQALSIQEGENATMNCSYKTSINNLQW YRQNSGRGLVHLILIRSNEREKHSGRLR VTLDTSKKSSSLLITASRAADTASYFCAT VSNYQLIWGAGTKLIIKPDIQNPDPAVYQ LRDSKSSDKSVCLFTDFDSQTNVSQSK DSDVYITDKTVLDMRSMDFKSNSAVAW SNKSDFACANAFNNSIIPEDTFFPSPES SCDVKLVEKSFETDTNLNFQNLSVIGFRI LLLKVAGFNLLMTLRLWSS |
| 7 | R36P3F9 | beta | CDR1 | MNHEY |
| 8 | R36P3F9 | beta | CDR2 | SMNVEV |
| 9 | R36P3F9 | beta | CDR3 | CASSSTSGGLSGETQYF |
| 10 | R36P3F9 | beta | variable domain | MGPQLLGYVVLCLLGAGPLEAQVTQNP RYLITVTGKKLTVTCSQNMNHEYMSWY RQDPGLGLRQIYYSMNVEVTDKGDVPE GYKVSRKEKRNFPLILESPSPNQTSLYF CASSSTSGGLSGETQYFGPGTRLLVL |
| 11 | R36P3F9 | beta | constant domain | EDLKNVFPPEVAVFEPSEAEISHTQKAT LVCLATGFYPDHVELSWWVNGKEVHS GVSTDPQPLKEQPALNDSRYCLSSRLR VSATFWQNPRNHFRCQVQFYGLSEND EWTQDRAKPVTQIVSAEAWGRADCGF TSESYQQGVLSATILYEILLGKATLYAVL VSALVLMAMVKRKDSRG |
| 12 | R36P3F9 | beta | full-length | MGPQLLGYVVLCLLGAGPLEAQVTQNP RYLITVTGKKLTVTCSQNMNHEYMSWY RQDPGLGLRQIYYSMNVEVTDKGDVPE GYKVSRKEKRNFPLILESPSPNQTSLYF CASSSTSGGLSGETQYFGPGTRLLVLE DLKNVFPPEVAVFEPSEAEISHTQKATL VCLATGFYPDHVELSWWVNGKEVHSG VSTDPQPLKEQPALNDSRYCLSSRLRV SATFWQNPRNHFRCQVQFYGLSENDE WTQDRAKPVTQIVSAEAWGRADCGFT SESYQQGVLSATILYEILLGKATLYAVLV SALVLMAMVKRKDSRG |
| 13 | R52P2G11 | alpha | CDR1 | VSPFSN |
| 14 | R52P2G11 | alpha | CDR2 | MTF |
| 15 | R52P2G11 | alpha | CDR3 | CVVSAYGKLQF |
| 16 | R52P2G11 | alpha | variable domain | MKKHLTTFLVILWLYFYRGNGKNQVEQ SPQSLIILEGKNCTLQCNYTVSPFSNLR WYKQDTRGRPVSLTIMTFSENTKSNGR YTATLDADTKQSSLHITASQLSDSASYIC VVSAYGKLQFGAGTQVVVTP |
| 17 | R52P2G11 | alpha | constant domain | DIQNPDPAVYQLRDSKSSDKSVCLFTDF DSQTNVSQSKDSDVYITDKTVLDMRSM DFKSNSAVAWSNKSDFACANAFNNSIIP EDTFFPSPESSCDVKLVEKSFETDTNLN FQNLSVIGFRILLLKVAGFNLLMTLRLWS S |

TABLE 1-continued

TCR sequences of the invention

| SEQ ID NO: | TCR name | Chain | Region | Sequence |
|---|---|---|---|---|
| 18 | R52P2G11 | alpha | full-length | MKKHLTTFLVILWLYFYRGNGKNQVEQ SPQSLIILEGKNCTLQCNYTVSPFSNLR WYKQDTGRGPVSLTIMTFSENTKSNGR YTATLDADTKQSSLHITASQLSDSASYIC VVSAYGKLQFGAGTQVVVTPDIQNPDP AVYQLRDSKSSDKSVCLFTDFDSQTNV SQSKDSDVYITDKTVLDMRSMDFKSNS AVAWSNKSDFACANAFNNSIIPEDTFFP SPESSCDVKLVEKSFETDTNLNFQNLSV IGFRILLLKVAGFNLLMTLRLWSS |
| 19 | R52P2G11 | beta | CDR1 | SGHNS |
| 20 | R52P2G11 | beta | CDR2 | FNNNVP |
| 21 | R52P2G11 | beta | CDR3 | CASSLGSPDGNQPQHF |
| 22 | R52P2G11 | beta | variable domain | MDSWTFCCVSLCILVAKHTDAGVIQSPR HEVTEMGQEVTLRCKPISGHNSLFWYR QTMMRGLELLIYFNNNVPIDDSGMPED RFSAKMPNASFSTLKIQPSEPRDSAVYF CASSLGSPDGNQPQHFGDGTRLSIL |
| 23 | R52P2G11 | beta | constant domain | EDLNKVFPPEVAVFEPSEAEISHTQKAT LVCLATGFFPDHVELSWWVNGKEVHS GVSTDPQPLKEQPALNDSRYCLSSRLR VSATFWQNPRNHFRCQVQFYGLSEND EWTQDRAKPVTQIVSAEAWGRADCGF TSVSYQQGVLSATILYEILLGKATLYAVL VSALVLMAMVKRKDF |
| 24 | R52P2G11 | beta | full-length | MDSWTFCCVSLCILVAKHTDAGVIQSPR HEVTEMGQEVTLRCKPISGHNSLFWYR QTMMRGLELLIYFNNNVPIDDSGMPED RFSAKMPNASFSTLKIQPSEPRDSAVYF CASSLGSPDGNQPQHFGDGTRLSILED LNKVFPPEVAVFEPSEAEISHTQKATLV CLATGFFPDHVELSWWVNGKEVHSGV STDPQPLKEQPALNDSRYCLSSRLRVS ATFWQNPRNHFRCQVQFYGLSENDEW TQDRAKPVTQIVSAEAWGRADCGFTSV SYQQGVLSATILYEILLGKATLYAVLVSA LVLMAMVKRKDF |
| 25 | R53P2A9 | alpha | CDR1 | TSESDYY |
| 26 | R53P2A9 | alpha | CDR2 | QEAY |
| 27 | R53P2A9 | alpha | CDR3 | CAYNSYAGGTSYGKLTF |
| 28 | R53P2A9 | alpha | variable domain | MACPGFLWALVISTCLEFSMAQTVTQS QPEMSVQEAETVTLSCTYDTSESDYYL FWYKQPPSRQMILVIRQEAYKQQNATE NRFSVNFQKAAKSFSLKISDSQLGDAA MYFCAYNSYAGGTSYGKLTFGQGTILT VHP |
| 29 | R53P2A9 | alpha | constant domain | NIQNPDPAVYQLRDSKSSDKSVCLFTDF DSQTNVSQSKDSDVYITDKTVLDMRSM DFKSNSAVAWSNKSDFACANAFNNSIIP EDTFFPSPESSCDVKLVEKSFETDTNLN FQNLSVIGFRILLLKVAGFNLLMTLRLWS S |
| 30 | R53P2A9 | alpha | full-length | MACPGFLWALVISTCLEFSMAQTVTQS QPEMSVQEAETVTLSCTYDTSESDYYL FWYKQPPSRQMILVIRQEAYKQQNATE NRFSVNFQKAAKSFSLKISDSQLGDAA MYFCAYNSYAGGTSYGKLTFGQGTILT VHPNIQNPDPAVYQLRDSKSSDKSVCL FTDFDSQTNVSQSKDSDVYITDKTVLD |

TABLE 1-continued

TCR sequences of the invention

| SEQ ID NO: | TCR name | Chain | Region | Sequence |
|---|---|---|---|---|
| | | | | MRSMDFKSNSAVAWSNKSDFACANAF NNSIIPEDTFFPSPESSCDVKLVEKSFET DTNLNFQNLSVIGFRILLLKVAGFNLLMT LRLWSS |
| 31 | R53P2A9 | beta | CDR1 | SGHKS |
| 32 | R53P2A9 | beta | CDR2 | YYEKEE |
| 33 | R53P2A9 | beta | CDR3 | CASSLDGTSEQYF |
| 34 | R53P2A9 | beta | variable domain | MGPGLLCWVLLCLLGAGPVDAGVTQSP THLIKTRGQQVTLRCSPISGHKSVSWY QQVLGQGPQFIFQYYEKEERGRGNFPD RFSARQFPNYSSELNVNALLLGDSALYL CASSLDGTSEQYFGPGTRLTVT |
| 35 | R53P2A9 | beta | constant domain | EDLKNVFPPEVAVFEPSEAEISHTQKAT LVCLATGFYPDHVELSWWVNGKEVHS GVSTDPQPLKEQPALNDSRYCLSSRLR VSATFWQNPRNHFRCQVQFYGLSEND EWTQDRAKPVTQIVSAEAWGRADCGF TSESYQQGVLSATILYEILLGKATLYAVL VSALVLMAMVKRKDSRG |
| 36 | R53P2A9 | beta | full-length | MGPGLLCWVLLCLLGAGPVDAGVTQSP THLIKTRGQQVTLRCSPISGHKSVSWY QQVLGQGPQFIFQYYEKEERGRGNFPD RFSARQFPNYSSELNVNALLLGDSALYL CASSLDGTSEQYFGPGTRLTVTEDLKN VFPPEVAVFEPSEAEISHTQKATLVCLA TGFYPDHVELSWWVNGKEVHSGVSTD PQPLKEQPALNDSRYCLSSRLRVSATF WQNPRNHFRCQVQFYGLSENDEWTQ DRAKPVTQIVSAEAWGRADCGFTSESY QQGVLSATILYEILLGKATLYAVLVSALV LMAMVKRKDSRG |
| 37 | 1G4 | alpha | CDR1 | DSAIYN |
| 38 | 1G4 | alpha | CDR2 | IQS |
| 39 | 1G4 | alpha | CDR3 | CAVRPTSGGSYIPTF |
| 40 | 1G4 | alpha | variable domain | METLLGLLILWLQLQWVSSKQEVTQIPA ALSVPEGENLVLNCSFTDSAIYNLQWFR QDPGKGLTSLLLIQSSREQTSGRLNA SLDKSSGRSTLYIAASQPGDSATYLCAV RPTSGGSYIPTFGRGTSLIVHP |
| 41 | 1G4 | alpha | constant domain | YIQNPDPAVYQLRDSKSSDKSVCLFTDF DSQTNVSQSKDSDVYITDKTVLDMRSM DFKSNSAVAWSNKSDFACANAFNNSIIP EDTFFPSPESSCDVKLVEKSFETDTNLN FQNLSVIGFRILLLKVAGFNLLMTLRLWS S |
| 42 | 1G4 | alpha | full-length | METLLGLLILWLQLQWVSSKQEVTQIPA ALSVPEGENLVLNCSFTDSAIYNLQWFR QDPGKGLTSLLLIQSSREQTSGRLNA SLDKSSGRSTLYIAASQPGDSATYLCAV RPTSGGSYIPTFGRGTSLIVHPYIQNPD PAVYQLRDSKSSDKSVCLFTDFDSQTN VSQSKDSDVYITDKTVLDMRSMDFKSN SAVAWSNKSDFACANAFNNSIIPEDTFF PSPESSCDVKLVEKSFETDTNLNFQNLS VIGFRILLLKVAGFNLLMTLRLWSS |
| 43 | 1G4 | beta | CDR1 | MNHEY |
| 44 | 1G4 | beta | CDR2 | SVGAGI |
| 45 | 1G4 | beta | CDR3 | CASSYVGNTGELFF |

TABLE 1-continued

TCR sequences of the invention

| SEQ ID NO: | TCR name | Chain | Region | Sequence |
|---|---|---|---|---|
| 46 | 1G4 | beta | variable domain | MSIGLLCCAALSLLWAGPVNAGVTQTP KFQVLKTGQSMTLQCAQDMNHEYMSW YRQDPGMGLRLIHYSVGAGITDQGEVP NGYNVSRSTTEDFPLRLLSAAPSQTSV YFCASSYVGNTGELFFGEGSRLTVL |
| 47 | 1G4 | beta | constant domain | EDLKNVFPPEVAVFEPSEAEISHTQKAT LVCLATGFYPDHVELSWWVNGKEVHS GVSTDPQPLKEQPALNDSRYCLSSRLR VSATFWQNPRNHFRCQVQFYGLSEND EWTQDRAKPVTQIVSAEAWGRADCGF TSESYQQGVLSATILYEILLGKATLYAVL VSALVLMAMVKRKDSRG |
| 48 | 1G4 | beta | full-length | MSIGLLCCAALSLLWAGPVNAGVTQTP KFQVLKTGQSMTLQCAQDMNHEYMSW YRQDPGMGLRLIHYSVGAGITDQGEVP NGYNVSRSTTEDFPLRLLSAAPSQTSV YFCASSYVGNTGELFFGEGSRLTVLED LKNVFPPEVAVFEPSEAEISHTQKATLV CLATGFYPDHVELSWWVNGKEVHSGV STDPQPLKEQPALNDSRYCLSSRLRVS ATFWQNPRNHFRCQVQFYGLSENDEW TQDRAKPVTQIVSAEAWGRADCGFTSE SYQQGVLSATILYEILLGKATLYAVLVSA LVLMAMVKRKDSRG |

TABLE 2

Peptide sequences of the invention and related sequences

| Peptide Code | Sequence | SEQ ID NO: |
|---|---|---|
| DCAF4L2-001 | ILQDGQFLV | 49 |
| DCAF4L2-001_A1 | ALQDGQFLV | 50 |
| DCAF4L2-001_A2 | IAQDGQFLV | 51 |
| DCAF4L2-001_A3 | ILADGQFLV | 52 |
| DCAF4L2-001_A4 | ILQAGQFLV | 53 |
| DCAF4L2-001_A5 | ILQDAQFLV | 54 |
| DCAF4L2-001_A6 | ILQDGAFLV | 55 |
| DCAF4L2-001_A7 | ILQDGQALV | 56 |
| DCAF4L2-001_A8 | ILQDGQFAV | 57 |
| DCAF4L2-001_A9 | ILQDGQFLA | 58 |
| GRB14-002 | GLVDGVFLV | 59 |
| SNR-004 | ILQDGRIFI | 60 |
| WRN-002 | ILQDLQPFL | 61 |
| MUC-009 | ILQEGTFKA | 62 |
| GSTA4-001 | KLQDGNHLL | 63 |
| PFN1-001 | LLQDGEFSM | 64 |
| VPS39-001 | LLQDKQFEL | 65 |
| AHR-002 | NLQEGEFLL | 66 |
| KCM-001 | TLQNSQFLL | 67 |
| VPS51-001 | TLTDEQFLV | 68 |
| NYESO1-001 | SLLMWITQV | 69 |
| DCAF4L2-001_T1 | TLQDGQFLV | 70 |
| DCAF4L2-001_T2 | ITQDGQFLV | 71 |
| DCAF4L2-001_T3 | ILTDGQFLV | 72 |
| DCAF4L2-001_T4 | ILQTGQFLV | 73 |
| DCAF4L2-001_T5 | ILQDTQFLV | 74 |
| DCAF4L2-001_T6 | ILQDGTFLV | 75 |
| DCAF4L2-001_T7 | ILQDGQTLV | 76 |
| DCAF4L2-001_T8 | ILQDGQFTV | 77 |
| DCAF4L2-001_T9 | ILQDGQFLT | 78 |

EXAMPLES

Background

Three DCAF4L2-001-specific TCRs (R36P3F9, R52P2G11 and R53P2A9, see Table 1), each encoding tumor specific TCR-alpha and TCR-beta chains, were isolated and amplified from T-cells of healthy donors. Cells from healthy donors were in vitro stimulated according to a method previously described (Walter et al., 2003 J Immunol., November 15; 171(10):4974-8) and target-specific cells were single-cell sorted using HLA-A*02 multimers and then used for subsequent TCR isolation. TCR sequences were isolated via 5' RACE by standard methods as described by e.g. Molecular Cloning a laboratory manual fourth edition by Green and Sambrook. The alpha and beta variable regions of TCRs R36P3F9, R52P2G11 and R53P2A9 were sequenced and expression constructs were generated by gene synthesis for further functional characterization. R36P3F9 is derived from HLA-A*02 positive donor and R52P2G11 and R53P2A9 are derived from a HLA-A*02 negative donor (allo-reactive setting).

TCRs of interest were expressed in human T cells by transduction e.g. through mRNA electroporation or lentiviral transduction. For lentiviral transduction, PBMC were thawed and rested overnight, and then activated using immobilized antibodies. Activated cells were transduced using a lentiviral vector encoding the DCAF4L2-specific TCR and expanded in the presence of cytokines. T cells were harvested and concentrated by centrifugation, then cryopreserved.

The T cells were assessed for IFN-γ release after co-culture with different target cells, such as T2 cells loaded with different peptides. Efficacy of CD8+ T cells expressing TCRs R52P2G11 and R53P2A9 was determined by e.g. T cell activation studies (IFNγ release) or killing assays using DCAF4L2-transduced A375 tumor cell line as target cells compared to non-modified A375 cells.

Example 1: T-Cell Receptor R36P3F9

TCR R36P3F9 (SEQ ID NO:1-12) is restricted towards HLA-A*02-presented DCAF4L2-001 (see FIG. 4).

R36P3F9 specifically recognizes DCAF4L2-001 as human primary CD8+ T-cells reexpressing this TCR release IFNγ upon co-incubation with HLA-A*02+ target cells loaded either with DCAF4L2-001 peptide or alanine substitution variants of DCAF4L2-001 (FIG. 1). TCR R36P3F9 does specifically recognize DCAF4L2-001, but not different peptides showing high degree of sequence similarity to DCAF4L2-001 (FIG. 4). NYESO1-001 peptide is used as negative control.

Target peptide titration analysis for R36P3F9 (FIG. 10) showed an EC50 in the range of 3.6 nM.

Example 2: T-Cell Receptor R52P2G11

TCR R52P2G11 (SEQ ID NO: 13-24) is restricted towards HLA-A*02-presented DCAF4L2-001 (see FIG. 5).

R52P2G11 specifically recognizes DCAF4L2-001 as human primary CD8+ T-cells reexpressing this TCR release IFNγ upon co-incubation with HLA-A*02+ target cells loaded either with DCAF4L2-001 peptide or alanine and threonine substitution variants of DCAF4L2-001 (FIGS. 2 and 11). TCR R52P2G11 does specifically recognize DCAF4L2-001, but not different peptides showing high degree of sequence similarity to DCAF4L2-001 (FIG. 5). NYESO1-001 peptide is used as negative control.

Re-expression of R52P2G11 leads to selective binding of HLA-A*02/DCAF4L2-001 tetramers but not HLA-A*02/NYESO1-001 tetramers in human primary CD8+ T-cells (FIG. 7). Re-expression of the NYESO1-001-specific TCR 1G4 and mock expression are used as control.

Target peptide titration analysis for R52P2G11 (FIG. 8) showed an EC50 in the range of ~8.5 nM.

Re-expression of R52P2G11 in human primary CD8+ T-cells leads to selective recognition of DCAF4L2-transduced A375 tumor cell line, but not non-modified A375 cells (FIG. 13). Non-transduced T cells are used as control. T-cell activation upon co-culture with cell lines expressing HLA-A*02 and DCAF4L2-001 reflects the recognition of endogenously presented target pHLA by TCRs R52P2G11 (FIG. 13).

Example 3: T-Cell Receptor R53P2A9

TCR R53P2A9 (SEQ ID NO: 25-36) is restricted towards HLA-A*02-presented DCAF4L2-001 (see FIG. 6 above).

R53P2A9 specifically recognizes DCAF4L2-001 as human primary CD8+ T-cells reexpressing this TCR release IFNγ upon co-incubation with HLA-A*02+ target cells loaded either with DCAF4L2-001 peptide or alanine and threonine substitution variants of DCAF4L2-001 (FIGS. 3 and 12). TCR R53P2A9 does specifically recognize DCAF4L2-001, but not different peptides showing high degree of sequence similarity to DCAF4L2-001 (FIG. 6). NYESO1-001 peptide is used as negative control.

Re-expression of R53P2A9 leads to selective binding of HLA-A*02/DCAF4L2-001 tetramers but not HLA-A*02/NYESO1-001 tetramers in human primary CD8+ T-cells (FIG. 7). Re-expression of the NYESO1-001-specific TCR 1G4 and mock expression are used as control.

Target peptide titration analysis for R53P2A9 (FIG. 9) showed an EC50 in the range of ~11.8 nM.

Re-expression of R53P2A9 in human primary CD8+ T-cells led to selective recognition of DCAF4L2-transduced A375 tumor cell line, but not non-modified A375 cells (FIG. 13). Non-transduced cells are used as control. T-cell activation upon co-culture with cell lines expressing HLA-A*02 and DCAF4L2-001 reflects the recognition of endogenously processed target pHLA by TCRs R53P2A9 (FIG. 13).

The invention claimed is:

1. A single chain TCR comprising:
a CDR1α chain comprising the amino acid sequence of SEQ ID NO: 25,
a CDR2α chain comprising the amino acid sequence of SEQ ID NO: 26;
a CDR3α chain comprising the amino acid sequence of SEQ ID NO: 27,
a CDR1β chain comprising the amino acid sequence of SEQ ID NO: 31,
a CDR2β chain comprising the amino acid sequence of SEQ ID NO: 32, and
a CDR3β chain comprising the amino acid sequence of SEQ ID NO: 33;
wherein said single chain TCR selectively binds to an epitope consisting of the amino acid sequence of SEQ ID NO: 49.

2. A pharmaceutical composition comprising the single chain TCR according to claim 1, and a pharmaceutical acceptable carrier, stabilizer and/or excipient.

3. The single chain TCR of claim 1, wherein said TCR is a soluble TCR.

4. The single chain TCR of claim 1, wherein the alpha chain comprises a TCR alpha variable domain comprising the amino acid sequence of SEQ ID NO: 28; and the beta chain comprises a TCR beta variable domain comprising the amino acid sequence of SEQ ID NO: 34.

5. A single chain TCR comprising:
a CDR1α chain consisting of SEQ ID NO: 25,
a CDR2α chain consisting of SEQ ID NO: 26,
a CDR3α chain consisting of SEQ ID NO: 27,
a CDR1β chain consisting of SEQ ID NO: 31,
a CDR2β chain consisting of SEQ ID NO: 32, and
a CDR3β chain consisting of SEQ ID NO: 33;
wherein said single chain TCR selectively binds to an epitope consisting of the amino acid sequence of SEQ ID NO: 49.

6. The single chain TCR of claim 5, comprising SEQ ID NO: 28.

7. The single chain TCR of claim 5, comprising SEQ ID NO: 34.

8. A single chain TCR comprising a TCR alpha variable domain consisting of the amino acid sequence of SEQ ID NO: 28; and a TCR beta variable domain consisting of the amino acid sequence of SEQ ID NO: 34, and wherein the TCR specifically binds to a TAA-peptide MHC molecule complex.

9. A single chain TCR comprising an alpha chain consisting of the amino acid sequence of SEQ ID NO: 30; and a beta chain consisting of the amino acid sequence of SEQ ID NO: 36, and wherein the TCR specifically binds to a TAA-peptide MHC molecule complex.

* * * * *

SEQUENCE LISTING

```
<160> NUMBER OF SEQ ID NOS: 78

<210> SEQ ID NO 1
<211> LENGTH: 5
<212> TYPE: PRT
<213> ORGANISM: Homo sapiens

<400> SEQUENCE: 1

Thr Ser Ile Asn Asn
1               5

<210> SEQ ID NO 2
<211> LENGTH: 3
```

```
<212> TYPE: PRT
<213> ORGANISM: Homo sapiens

<400> SEQUENCE: 2

Ile Arg Ser
1

<210> SEQ ID NO 3
<211> LENGTH: 11
<212> TYPE: PRT
<213> ORGANISM: Homo sapiens

<400> SEQUENCE: 3

Cys Ala Thr Val Ser Asn Tyr Gln Leu Ile Trp
1               5                   10

<210> SEQ ID NO 4
<211> LENGTH: 129
<212> TYPE: PRT
<213> ORGANISM: Homo sapiens

<400> SEQUENCE: 4

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Leu Leu Ile
            85                  90                  95

Thr Ala Ser Arg Ala Ala Asp Thr Ala Ser Tyr Phe Cys Ala Thr Val
            100                 105                 110

Ser Asn Tyr Gln Leu Ile Trp Gly Ala Gly Thr Lys Leu Ile Ile Lys
        115                 120                 125

Pro

<210> SEQ ID NO 5
<211> LENGTH: 141
<212> TYPE: PRT
<213> ORGANISM: Homo sapiens

<400> SEQUENCE: 5

Asp Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
            85                  90                  95
```

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
            115                 120                 125

Gly Phe Asn Leu Leu Met Thr Leu Arg Leu Trp Ser Ser
130                 135                 140

<210> SEQ ID NO 6
<211> LENGTH: 270
<212> TYPE: PRT
<213> ORGANISM: Homo sapiens

<400> SEQUENCE: 6

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Ser Leu Leu Ile
                85                  90                  95

Thr Ala Ser Arg Ala Ala Asp Thr Ala Ser Tyr Phe Cys Ala Thr Val
            100                 105                 110

Ser Asn Tyr Gln Leu Ile Trp Gly Ala Gly Thr Lys Leu Ile Ile Lys
            115                 120                 125

Pro Asp Ile Gln Asn Pro Asp Pro Ala Val Tyr Gln Leu Arg Asp Ser
        130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
            195                 200                 205

Ser Ile Ile Pro Glu Asp Thr Phe Phe Pro Ser Pro Glu Ser Ser Cys
        210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270

<210> SEQ ID NO 7
<211> LENGTH: 5
<212> TYPE: PRT
<213> ORGANISM: Homo sapiens

<400> SEQUENCE: 7

Met Asn His Glu Tyr
1               5

```
<210> SEQ ID NO 8
<211> LENGTH: 6
<212> TYPE: PRT
<213> ORGANISM: Homo sapiens

<400> SEQUENCE: 8

Ser Met Asn Val Glu Val
1               5

<210> SEQ ID NO 9
<211> LENGTH: 17
<212> TYPE: PRT
<213> ORGANISM: Homo sapiens

<400> SEQUENCE: 9

Cys Ala Ser Ser Thr Ser Gly Gly Leu Ser Gly Glu Thr Gln Tyr
1               5                   10                  15

Phe

<210> SEQ ID NO 10
<211> LENGTH: 135
<212> TYPE: PRT
<213> ORGANISM: Homo sapiens

<400> SEQUENCE: 10

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
                100                 105                 110

Ser Ser Thr Ser Gly Gly Leu Ser Gly Glu Thr Gln Tyr Phe Gly Pro
        115                 120                 125

Gly Thr Arg Leu Leu Val Leu
        130                 135

<210> SEQ ID NO 11
<211> LENGTH: 179
<212> TYPE: PRT
<213> ORGANISM: Homo sapiens

<400> SEQUENCE: 11

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60
```

```
Glu Gln Pro Ala Leu Asn Asp Ser Arg Tyr Cys Leu Ser Ser Arg Leu
 65                  70                  75                  80

Arg Val Ser Ala Thr Phe Trp Gln Asn Pro Arg Asn His Phe Arg Cys
                 85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 12
<211> LENGTH: 314
<212> TYPE: PRT
<213> ORGANISM: Homo sapiens

<400> SEQUENCE: 12

Met Gly Pro Gln Leu Leu Gly Tyr Val Val Leu Cys Leu Leu Gly Ala
  1               5                  10                  15

Gly Pro Leu Glu Ala Gln Val Thr Gln Asn Pro Arg Tyr Leu Ile Thr
                 20                  25                  30

Val Thr Gly Lys Lys Leu Thr Val Thr Cys Ser Gln Asn Met Asn His
             35                  40                  45

Glu Tyr Met Ser Trp Tyr Arg Gln Asp Pro Gly Leu Gly Leu Arg Gln
 50                  55                  60

Ile Tyr Tyr Ser Met Asn Val Glu Val Thr Asp Lys Gly Asp Val Pro
 65                  70                  75                  80

Glu Gly Tyr Lys Val Ser Arg Lys Glu Lys Arg Asn Phe Pro Leu Ile
                 85                  90                  95

Leu Glu Ser Pro Ser Pro Asn Gln Thr Ser Leu Tyr Phe Cys Ala Ser
            100                 105                 110

Ser Ser Thr Ser Gly Gly Leu Ser Gly Glu Thr Gln Tyr Phe Gly Pro
        115                 120                 125

Gly Thr Arg Leu Leu Val Leu Glu Asp Leu Lys Asn Val Phe Pro Pro
    130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255
```

Ser Ala Glu Ala Trp Gly Arg Ala Asp Cys Gly Phe Thr Ser Glu Ser
                260                 265                 270

Tyr Gln Gln Gly Val Leu Ser Ala Thr Ile Leu Tyr Glu Ile Leu Leu
            275                 280                 285

Gly Lys Ala Thr Leu Tyr Ala Val Leu Val Ser Ala Leu Val Leu Met
    290                 295                 300

Ala Met Val Lys Arg Lys Asp Ser Arg Gly
305                 310

<210> SEQ ID NO 13
<211> LENGTH: 6
<212> TYPE: PRT
<213> ORGANISM: Homo sapiens

<400> SEQUENCE: 13

Val Ser Pro Phe Ser Asn
1               5

<210> SEQ ID NO 14
<211> LENGTH: 3
<212> TYPE: PRT
<213> ORGANISM: Homo sapiens

<400> SEQUENCE: 14

Met Thr Phe
1

<210> SEQ ID NO 15
<211> LENGTH: 11
<212> TYPE: PRT
<213> ORGANISM: Homo sapiens

<400> SEQUENCE: 15

Cys Val Val Ser Ala Tyr Gly Lys Leu Gln Phe
1               5                   10

<210> SEQ ID NO 16
<211> LENGTH: 131
<212> TYPE: PRT
<213> ORGANISM: Homo sapiens

<400> SEQUENCE: 16

Met Lys Lys His Leu Thr Thr Phe Leu Val Ile Leu Trp Leu Tyr Phe
1               5                   10                  15

Tyr Arg Gly Asn Gly Lys Asn Gln Val Glu Gln Ser Pro Gln Ser Leu
            20                  25                  30

Ile Ile Leu Glu Gly Lys Asn Cys Thr Leu Gln Cys Asn Tyr Thr Val
        35                  40                  45

Ser Pro Phe Ser Asn Leu Arg Trp Tyr Lys Gln Asp Thr Gly Arg Gly
    50                  55                  60

Pro Val Ser Leu Thr Ile Met Thr Phe Ser Glu Asn Thr Lys Ser Asn
65                  70                  75                  80

Gly Arg Tyr Thr Ala Thr Leu Asp Ala Asp Thr Lys Gln Ser Ser Leu
                85                  90                  95

His Ile Thr Ala Ser Gln Leu Ser Asp Ser Ala Ser Tyr Ile Cys Val
            100                 105                 110

Val Ser Ala Tyr Gly Lys Leu Gln Phe Gly Ala Gly Thr Gln Val Val
        115                 120                 125

Val Thr Pro
    130

<210> SEQ ID NO 17
<211> LENGTH: 141
<212> TYPE: PRT
<213> ORGANISM: Homo sapiens

<400> SEQUENCE: 17

Asp Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 18
<211> LENGTH: 272
<212> TYPE: PRT
<213> ORGANISM: Homo sapiens

<400> SEQUENCE: 18

Met Lys Lys His Leu Thr Thr Phe Leu Val Ile Leu Trp Leu Tyr Phe
1               5                   10                  15

Tyr Arg Gly Asn Gly Lys Asn Gln Val Glu Gln Ser Pro Gln Ser Leu
            20                  25                  30

Ile Ile Leu Glu Gly Lys Asn Cys Thr Leu Gln Cys Asn Tyr Thr Val
        35                  40                  45

Ser Pro Phe Ser Asn Leu Arg Trp Tyr Lys Gln Asp Thr Gly Arg Gly
    50                  55                  60

Pro Val Ser Leu Thr Ile Met Thr Phe Ser Glu Asn Thr Lys Ser Asn
65                  70                  75                  80

Gly Arg Tyr Thr Ala Thr Leu Asp Ala Asp Thr Lys Gln Ser Ser Leu
                85                  90                  95

His Ile Thr Ala Ser Gln Leu Ser Asp Ser Ala Ser Tyr Ile Cys Val
            100                 105                 110

Val Ser Ala Tyr Gly Lys Leu Gln Phe Gly Ala Gly Thr Gln Val Val
        115                 120                 125

Val Thr Pro Asp Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

-continued

```
Ala Val Ala Trp Ser Asn Lys Ser Asp Phe Ala Cys Ala Asn Ala Phe
            195                 200                 205

Asn Asn Ser Ile Ile Pro Glu Asp Thr Phe Phe Pro Ser Pro Glu Ser
            210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
            245                 250                 255

Lys Val Ala Gly Phe Asn Leu Leu Met Thr Leu Arg Leu Trp Ser Ser
            260                 265                 270

<210> SEQ ID NO 19
<211> LENGTH: 5
<212> TYPE: PRT
<213> ORGANISM: Homo sapiens

<400> SEQUENCE: 19

Ser Gly His Asn Ser
1               5

<210> SEQ ID NO 20
<211> LENGTH: 6
<212> TYPE: PRT
<213> ORGANISM: Homo sapiens

<400> SEQUENCE: 20

Phe Asn Asn Asn Val Pro
1               5

<210> SEQ ID NO 21
<211> LENGTH: 16
<212> TYPE: PRT
<213> ORGANISM: Homo sapiens

<400> SEQUENCE: 21

Cys Ala Ser Ser Leu Gly Ser Pro Asp Gly Asn Gln Pro Gln His Phe
1               5                   10                  15

<210> SEQ ID NO 22
<211> LENGTH: 135
<212> TYPE: PRT
<213> ORGANISM: Homo sapiens

<400> SEQUENCE: 22

Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asn Ser Leu Phe Trp Tyr Arg Gln Thr Met Met Arg Gly Leu Glu Leu
    50                  55                  60

Leu Ile Tyr Phe Asn Asn Asn Val Pro Ile Asp Ser Gly Met Pro
65                  70                  75                  80

Glu Asp Arg Phe Ser Ala Lys Met Pro Asn Ala Ser Phe Ser Thr Leu
            85                  90                  95

Lys Ile Gln Pro Ser Glu Pro Arg Asp Ser Ala Val Tyr Phe Cys Ala
            100                 105                 110

Ser Ser Leu Gly Ser Pro Asp Gly Asn Gln Pro Gln His Phe Gly Asp
```

```
            115                 120                 125

Gly Thr Arg Leu Ser Ile Leu
    130                 135

<210> SEQ ID NO 23
<211> LENGTH: 177
<212> TYPE: PRT
<213> ORGANISM: Homo sapiens

<400> SEQUENCE: 23

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 24
<211> LENGTH: 312
<212> TYPE: PRT
<213> ORGANISM: Homo sapiens

<400> SEQUENCE: 24

Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asn Ser Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Leu Gly Ser Pro Asp Gly Asn Gln Pro Gln His Phe Gly Asp
        115                 120                 125
```

```
Gly Thr Arg Leu Ser Ile Leu Glu Asp Leu Asn Lys Val Phe Pro Pro
    130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Phe Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Val Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
290                 295                 300

Ala Met Val Lys Arg Lys Asp Phe
305                 310
```

<210> SEQ ID NO 25
<211> LENGTH: 7
<212> TYPE: PRT
<213> ORGANISM: Homo sapiens

<400> SEQUENCE: 25

```
Thr Ser Glu Ser Asp Tyr Tyr
1               5
```

<210> SEQ ID NO 26
<211> LENGTH: 4
<212> TYPE: PRT
<213> ORGANISM: Homo sapiens

<400> SEQUENCE: 26

```
Gln Glu Ala Tyr
1
```

<210> SEQ ID NO 27
<211> LENGTH: 17
<212> TYPE: PRT
<213> ORGANISM: Homo sapiens

<400> SEQUENCE: 27

```
Cys Ala Tyr Asn Ser Tyr Ala Gly Gly Thr Ser Tyr Gly Lys Leu Thr
1               5                   10                  15

Phe
```

<210> SEQ ID NO 28
<211> LENGTH: 138
<212> TYPE: PRT
<213> ORGANISM: Homo sapiens

<400> SEQUENCE: 28

```
Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Ser Asp Tyr Tyr Leu Phe Trp Tyr Lys Gln Pro Pro Ser Arg Gln
    50                  55                  60

Met Ile Leu Val Ile Arg Gln Glu Ala Tyr Lys Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Tyr Asn Ser Tyr Ala Gly Gly Thr Ser Tyr Gly Lys Leu Thr Phe
        115                 120                 125

Gly Gln Gly Thr Ile Leu Thr Val His Pro
    130                 135

<210> SEQ ID NO 29
<211> LENGTH: 141
<212> TYPE: PRT
<213> ORGANISM: Homo sapiens

<400> SEQUENCE: 29

Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 30
<211> LENGTH: 279
<212> TYPE: PRT
<213> ORGANISM: Homo sapiens

<400> SEQUENCE: 30

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45
```

```
Glu Ser Asp Tyr Tyr Leu Phe Trp Tyr Lys Gln Pro Pro Ser Arg Gln
     50                  55                  60

Met Ile Leu Val Ile Arg Gln Glu Ala Tyr Lys Gln Gln Asn Ala Thr
 65                  70                  75                  80

Glu Asn Arg Phe Ser Val Asn Phe Gln Lys Ala Ala Lys Ser Phe Ser
                 85                  90                  95

Leu Lys Ile Ser Asp Ser Gln Leu Gly Asp Ala Ala Met Tyr Phe Cys
             100                 105                 110

Ala Tyr Asn Ser Tyr Ala Gly Gly Thr Ser Tyr Gly Lys Leu Thr Phe
         115                 120                 125

Gly Gln Gly Thr Ile Leu Thr Val His Pro Asn Ile Gln Asn Pro Asp
     130                 135                 140

Pro Ala Val Tyr Gln Leu Arg Asp Ser Lys Ser Ser Asp Lys Ser Val
145                 150                 155                 160

Cys Leu Phe Thr Asp Phe Asp Ser Gln Thr Asn Val Ser Gln Ser Lys
                 165                 170                 175

Asp Ser Asp Val Tyr Ile Thr Asp Lys Thr Val Leu Asp Met Arg Ser
             180                 185                 190

Met Asp Phe Lys Ser Asn Ser Ala Val Ala Trp Ser Asn Lys Ser Asp
         195                 200                 205

Phe Ala Cys Ala Asn Ala Phe Asn Asn Ser Ile Ile Pro Glu Asp Thr
     210                 215                 220

Phe Phe Pro Ser Pro Glu Ser Ser Cys Asp Val Lys Leu Val Glu Lys
225                 230                 235                 240

Ser Phe Glu Thr Asp Thr Asn Leu Asn Phe Gln Asn Leu Ser Val Ile
                 245                 250                 255

Gly Phe Arg Ile Leu Leu Leu Lys Val Ala Gly Phe Asn Leu Leu Met
             260                 265                 270

Thr Leu Arg Leu Trp Ser Ser
         275

<210> SEQ ID NO 31
<211> LENGTH: 5
<212> TYPE: PRT
<213> ORGANISM: Homo sapiens

<400> SEQUENCE: 31

Ser Gly His Lys Ser
1               5

<210> SEQ ID NO 32
<211> LENGTH: 6
<212> TYPE: PRT
<213> ORGANISM: Homo sapiens

<400> SEQUENCE: 32

Tyr Tyr Glu Lys Glu Glu
1               5

<210> SEQ ID NO 33
<211> LENGTH: 13
<212> TYPE: PRT
<213> ORGANISM: Homo sapiens

<400> SEQUENCE: 33

Cys Ala Ser Ser Leu Asp Gly Thr Ser Glu Gln Tyr Phe
1               5                   10
```

<210> SEQ ID NO 34
<211> LENGTH: 131
<212> TYPE: PRT
<213> ORGANISM: Homo sapiens

<400> SEQUENCE: 34

Met Gly Pro Gly Leu Cys Trp Val Leu Cys Leu Leu Gly Ala
1               5                   10                  15

Gly Pro Val Asp Ala Gly Val Thr Gln Ser Pro Thr His Leu Ile Lys
            20                  25                  30

Thr Arg Gly Gln Gln Val Thr Leu Arg Cys Ser Pro Ile Ser Gly His
        35                  40                  45

Lys Ser Val Ser Trp Tyr Gln Gln Val Leu Gly Gln Gly Pro Gln Phe
    50                  55                  60

Ile Phe Gln Tyr Tyr Glu Lys Glu Glu Arg Gly Arg Gly Asn Phe Pro
65                  70                  75                  80

Asp Arg Phe Ser Ala Arg Gln Phe Pro Asn Tyr Ser Ser Glu Leu Asn
                85                  90                  95

Val Asn Ala Leu Leu Leu Gly Asp Ser Ala Leu Tyr Leu Cys Ala Ser
            100                 105                 110

Ser Leu Asp Gly Thr Ser Glu Gln Tyr Phe Gly Pro Gly Thr Arg Leu
        115                 120                 125

Thr Val Thr
    130

<210> SEQ ID NO 35
<211> LENGTH: 179
<212> TYPE: PRT
<213> ORGANISM: Homo sapiens

<400> SEQUENCE: 35

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

```
<210> SEQ ID NO 36
<211> LENGTH: 310
<212> TYPE: PRT
<213> ORGANISM: Homo sapiens

<400> SEQUENCE: 36

Met Gly Pro Gly Leu Leu Cys Trp Val Leu Leu Cys Leu Leu Gly Ala
1               5                   10                  15

Gly Pro Val Asp Ala Gly Val Thr Gln Ser Pro Thr His Leu Ile Lys
            20                  25                  30

Thr Arg Gly Gln Gln Val Thr Leu Arg Cys Ser Pro Ile Ser Gly His
        35                  40                  45

Lys Ser Val Ser Trp Tyr Gln Gln Val Leu Gly Gln Gly Pro Gln Phe
    50                  55                  60

Ile Phe Gln Tyr Tyr Glu Lys Glu Glu Arg Gly Arg Gly Asn Phe Pro
65                  70                  75                  80

Asp Arg Phe Ser Ala Arg Gln Phe Pro Asn Tyr Ser Ser Glu Leu Asn
                85                  90                  95

Val Asn Ala Leu Leu Leu Gly Asp Ser Ala Leu Tyr Leu Cys Ala Ser
            100                 105                 110

Ser Leu Asp Gly Thr Ser Glu Gln Tyr Phe Gly Pro Gly Thr Arg Leu
        115                 120                 125

Thr Val Thr Glu Asp Leu Lys Asn Val Phe Pro Pro Glu Val Ala Val
130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Ser Arg Gly
305                 310

<210> SEQ ID NO 37
<211> LENGTH: 6
<212> TYPE: PRT
<213> ORGANISM: Homo sapiens

<400> SEQUENCE: 37

Asp Ser Ala Ile Tyr Asn
1               5
```

```
<210> SEQ ID NO 38
<211> LENGTH: 3
<212> TYPE: PRT
<213> ORGANISM: Homo sapiens

<400> SEQUENCE: 38

Ile Gln Ser
1

<210> SEQ ID NO 39
<211> LENGTH: 15
<212> TYPE: PRT
<213> ORGANISM: Homo sapiens

<400> SEQUENCE: 39

Cys Ala Val Arg Pro Thr Ser Gly Gly Ser Tyr Ile Pro Thr Phe
1               5                   10                  15

<210> SEQ ID NO 40
<211> LENGTH: 133
<212> TYPE: PRT
<213> ORGANISM: Homo sapiens

<400> SEQUENCE: 40

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
                20                  25                  30

Pro Glu Gly Glu Asn Leu Val Leu Asn Cys Ser Phe Thr Asp Ser Ala
            35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Arg
            100                 105                 110

Pro Thr Ser Gly Gly Ser Tyr Ile Pro Thr Phe Gly Arg Gly Thr Ser
        115                 120                 125

Leu Ile Val His Pro
        130

<210> SEQ ID NO 41
<211> LENGTH: 141
<212> TYPE: PRT
<213> ORGANISM: Homo sapiens

<400> SEQUENCE: 41

Tyr Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
                20                  25                  30

Asn Val Ser Gln Ser Lys Asp Ser Asp Val Tyr Ile Thr Asp Lys Thr
            35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80
```

```
Ile Ile Pro Glu Asp Thr Phe Phe Pro Ser Pro Glu Ser Ser Cys Asp
             85                  90                  95

Val Lys Leu Val Glu Lys Ser Phe Glu Thr Asp Thr Asn Leu Asn Phe
        100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
130                 135                 140
```

<210> SEQ ID NO 42
<211> LENGTH: 274
<212> TYPE: PRT
<213> ORGANISM: Homo sapiens

<400> SEQUENCE: 42

```
Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Arg
            100                 105                 110

Pro Thr Ser Gly Gly Ser Tyr Ile Pro Thr Phe Gly Arg Gly Thr Ser
        115                 120                 125

Leu Ile Val His Pro Tyr Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser
```

<210> SEQ ID NO 43
<211> LENGTH: 5
<212> TYPE: PRT
<213> ORGANISM: Homo sapiens

```
<400> SEQUENCE: 43

Met Asn His Glu Tyr
1               5

<210> SEQ ID NO 44
<211> LENGTH: 6
<212> TYPE: PRT
<213> ORGANISM: Homo sapiens

<400> SEQUENCE: 44

Ser Val Gly Ala Gly Ile
1               5

<210> SEQ ID NO 45
<211> LENGTH: 14
<212> TYPE: PRT
<213> ORGANISM: Homo sapiens

<400> SEQUENCE: 45

Cys Ala Ser Ser Tyr Val Gly Asn Thr Gly Glu Leu Phe Phe
1               5                  10

<210> SEQ ID NO 46
<211> LENGTH: 132
<212> TYPE: PRT
<213> ORGANISM: Homo sapiens

<400> SEQUENCE: 46

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
                20                  25                  30

Lys Thr Gly Gln Ser Met Thr Leu Gln Cys Ala Gln Asp Met Asn His
            35                  40                  45

Glu Tyr Met Ser Trp Tyr Arg Gln Asp Pro Gly Met Gly Leu Arg Leu
        50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Tyr Val Gly Asn Thr Gly Glu Leu Phe Phe Gly Glu Gly Ser Arg
        115                 120                 125

Leu Thr Val Leu
    130

<210> SEQ ID NO 47
<211> LENGTH: 179
<212> TYPE: PRT
<213> ORGANISM: Homo sapiens

<400> SEQUENCE: 47

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
                20                  25                  30

Ala Thr Gly Phe Tyr Pro Asp His Val Glu Leu Ser Trp Trp Val Asn
            35                  40                  45
```

```
Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly
```

<210> SEQ ID NO 48
<211> LENGTH: 311
<212> TYPE: PRT
<213> ORGANISM: Homo sapiens

<400> SEQUENCE: 48

```
Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
                20                  25                  30

Lys Thr Gly Gln Ser Met Thr Leu Gln Cys Ala Gln Asp Met Asn His
            35                  40                  45

Glu Tyr Met Ser Trp Tyr Arg Gln Asp Pro Gly Met Gly Leu Arg Leu
        50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Tyr Val Gly Asn Thr Gly Glu Leu Phe Phe Gly Glu Gly Ser Arg
        115                 120                 125

Leu Thr Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240
```

Trp Thr Gln Asp Arg Ala Lys Pro Val Thr Gln Ile Val Ser Ala Glu
            245                 250                 255

Ala Trp Gly Arg Ala Asp Cys Gly Phe Thr Ser Glu Ser Tyr Gln Gln
        260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
        290                 295                 300

Lys Arg Lys Asp Ser Arg Gly
305                 310

<210> SEQ ID NO 49
<211> LENGTH: 9
<212> TYPE: PRT
<213> ORGANISM: Homo sapiens

<400> SEQUENCE: 49

Ile Leu Gln Asp Gly Gln Phe Leu Val
1               5

<210> SEQ ID NO 50
<211> LENGTH: 9
<212> TYPE: PRT
<213> ORGANISM: Homo sapiens

<400> SEQUENCE: 50

Ala Leu Gln Asp Gly Gln Phe Leu Val
1               5

<210> SEQ ID NO 51
<211> LENGTH: 9
<212> TYPE: PRT
<213> ORGANISM: Homo sapiens

<400> SEQUENCE: 51

Ile Ala Gln Asp Gly Gln Phe Leu Val
1               5

<210> SEQ ID NO 52
<211> LENGTH: 9
<212> TYPE: PRT
<213> ORGANISM: Homo sapiens

<400> SEQUENCE: 52

Ile Leu Ala Asp Gly Gln Phe Leu Val
1               5

<210> SEQ ID NO 53
<211> LENGTH: 9
<212> TYPE: PRT
<213> ORGANISM: Homo sapiens

<400> SEQUENCE: 53

Ile Leu Gln Ala Gly Gln Phe Leu Val
1               5

<210> SEQ ID NO 54
<211> LENGTH: 9
<212> TYPE: PRT
<213> ORGANISM: Homo sapiens

<400> SEQUENCE: 54

Ile Leu Gln Asp Ala Gln Phe Leu Val

<210> SEQ ID NO 55
<211> LENGTH: 9
<212> TYPE: PRT
<213> ORGANISM: Homo sapiens

<400> SEQUENCE: 55

Ile Leu Gln Asp Gly Ala Phe Leu Val
1               5

<210> SEQ ID NO 56
<211> LENGTH: 9
<212> TYPE: PRT
<213> ORGANISM: Homo sapiens

<400> SEQUENCE: 56

Ile Leu Gln Asp Gly Gln Ala Leu Val
1               5

<210> SEQ ID NO 57
<211> LENGTH: 9
<212> TYPE: PRT
<213> ORGANISM: Homo sapiens

<400> SEQUENCE: 57

Ile Leu Gln Asp Gly Gln Phe Ala Val
1               5

<210> SEQ ID NO 58
<211> LENGTH: 9
<212> TYPE: PRT
<213> ORGANISM: Homo sapiens

<400> SEQUENCE: 58

Ile Leu Gln Asp Gly Gln Phe Leu Ala
1               5

<210> SEQ ID NO 59
<211> LENGTH: 9
<212> TYPE: PRT
<213> ORGANISM: Homo sapiens

<400> SEQUENCE: 59

Gly Leu Val Asp Gly Val Phe Leu Val
1               5

<210> SEQ ID NO 60
<211> LENGTH: 9
<212> TYPE: PRT
<213> ORGANISM: Homo sapiens

<400> SEQUENCE: 60

Ile Leu Gln Asp Gly Arg Ile Phe Ile
1               5

<210> SEQ ID NO 61
<211> LENGTH: 9
<212> TYPE: PRT
<213> ORGANISM: Homo sapiens

<400> SEQUENCE: 61

Ile Leu Gln Asp Leu Gln Pro Phe Leu
1               5

```
<210> SEQ ID NO 62
<211> LENGTH: 9
<212> TYPE: PRT
<213> ORGANISM: Homo sapiens

<400> SEQUENCE: 62

Ile Leu Gln Glu Gly Thr Phe Lys Ala
1               5

<210> SEQ ID NO 63
<211> LENGTH: 9
<212> TYPE: PRT
<213> ORGANISM: Homo sapiens

<400> SEQUENCE: 63

Lys Leu Gln Asp Gly Asn His Leu Leu
1               5

<210> SEQ ID NO 64
<211> LENGTH: 9
<212> TYPE: PRT
<213> ORGANISM: Homo sapiens

<400> SEQUENCE: 64

Leu Leu Gln Asp Gly Glu Phe Ser Met
1               5

<210> SEQ ID NO 65
<211> LENGTH: 9
<212> TYPE: PRT
<213> ORGANISM: Homo sapiens

<400> SEQUENCE: 65

Leu Leu Gln Asp Lys Gln Phe Glu Leu
1               5

<210> SEQ ID NO 66
<211> LENGTH: 9
<212> TYPE: PRT
<213> ORGANISM: Homo sapiens

<400> SEQUENCE: 66

Asn Leu Gln Glu Gly Glu Phe Leu Leu
1               5

<210> SEQ ID NO 67
<211> LENGTH: 9
<212> TYPE: PRT
<213> ORGANISM: Homo sapiens

<400> SEQUENCE: 67

Thr Leu Gln Asn Ser Gln Phe Leu Leu
1               5

<210> SEQ ID NO 68
<211> LENGTH: 9
<212> TYPE: PRT
<213> ORGANISM: Homo sapiens

<400> SEQUENCE: 68

Thr Leu Thr Asp Glu Gln Phe Leu Val
1               5

<210> SEQ ID NO 69
```

```
<211> LENGTH: 9
<212> TYPE: PRT
<213> ORGANISM: Homo sapiens

<400> SEQUENCE: 69

Ser Leu Leu Met Trp Ile Thr Gln Val
1               5

<210> SEQ ID NO 70
<211> LENGTH: 9
<212> TYPE: PRT
<213> ORGANISM: Homo sapiens

<400> SEQUENCE: 70

Thr Leu Gln Asp Gly Gln Phe Leu Val
1               5

<210> SEQ ID NO 71
<211> LENGTH: 9
<212> TYPE: PRT
<213> ORGANISM: Homo sapiens

<400> SEQUENCE: 71

Ile Thr Gln Asp Gly Gln Phe Leu Val
1               5

<210> SEQ ID NO 72
<211> LENGTH: 9
<212> TYPE: PRT
<213> ORGANISM: Homo sapiens

<400> SEQUENCE: 72

Ile Leu Thr Asp Gly Gln Phe Leu Val
1               5

<210> SEQ ID NO 73
<211> LENGTH: 9
<212> TYPE: PRT
<213> ORGANISM: Homo sapiens

<400> SEQUENCE: 73

Ile Leu Gln Thr Gly Gln Phe Leu Val
1               5

<210> SEQ ID NO 74
<211> LENGTH: 9
<212> TYPE: PRT
<213> ORGANISM: Homo sapiens

<400> SEQUENCE: 74

Ile Leu Gln Asp Thr Gln Phe Leu Val
1               5

<210> SEQ ID NO 75
<211> LENGTH: 9
<212> TYPE: PRT
<213> ORGANISM: Homo sapiens

<400> SEQUENCE: 75

Ile Leu Gln Asp Gly Thr Phe Leu Val
1               5

<210> SEQ ID NO 76
<211> LENGTH: 9
<212> TYPE: PRT
```

```
<213> ORGANISM: Homo sapiens

<400> SEQUENCE: 76

Ile Leu Gln Asp Gly Gln Thr Leu Val
1               5

<210> SEQ ID NO 77
<211> LENGTH: 9
<212> TYPE: PRT
<213> ORGANISM: Homo sapiens

<400> SEQUENCE: 77

Ile Leu Gln Asp Gly Gln Phe Thr Val
1               5

<210> SEQ ID NO 78
<211> LENGTH: 9
<212> TYPE: PRT
<213> ORGANISM: Homo sapiens

<400> SEQUENCE: 78

Ile Leu Gln Asp Gly Gln Phe Leu Thr
1               5
```